US010028766B2

(12) United States Patent
Nakagawa et al.

(10) Patent No.: US 10,028,766 B2
(45) Date of Patent: Jul. 24, 2018

(54) JET STREAM GENERATING DEVICE AND JET STREAM GENERATING METHOD

(71) Applicant: Tohoku University, Miyagi (JP)

(72) Inventors: Atsuhiro Nakagawa, Miyagi (JP); Teiji Tominaga, Miyagi (JP); Michihiro Kaneda, Tokyo (JP)

(73) Assignee: Tohoku University, Miyagi (JP)

( * ) Notice: Subject to any disclaimer, the term of this patent is extended or adjusted under 35 U.S.C. 154(b) by 30 days.

(21) Appl. No.: 15/119,858

(22) PCT Filed: Dec. 17, 2014

(86) PCT No.: PCT/JP2014/083358
§ 371 (c)(1),
(2) Date: Aug. 18, 2016

(87) PCT Pub. No.: WO2015/125394
PCT Pub. Date: Aug. 27, 2015

(65) Prior Publication Data
US 2017/0056042 A1    Mar. 2, 2017

(30) Foreign Application Priority Data
Feb. 18, 2014  (JP) ................................. 2014-029014

(51) Int. Cl.
*B05B 17/00* (2006.01)
*A61B 17/3203* (2006.01)
(Continued)

(52) U.S. Cl.
CPC ...... *A61B 17/3203* (2013.01); *A61B 1/00087* (2013.01); *A61B 1/015* (2013.01);
(Continued)

(58) Field of Classification Search
CPC . A61B 17/3203; A61B 1/00087; A61B 1/015; A61B 17/295; B05B 7/16; B05B 9/002; B05B 12/06; B05B 7/2408
(Continued)

(56) References Cited
U.S. PATENT DOCUMENTS 4,597,380 A * 7/1986 Raif .................... A61B 18/201
606/14
6,117,128 A * 9/2000 Gregory ................ A61B 18/24
607/89
(Continued)

FOREIGN PATENT DOCUMENTS

| JP | 2003-111766 A | 4/2003 |
|---|---|---|
| JP | 2005-152094 A | 6/2005 |

(Continued)

OTHER PUBLICATIONS

International Search Report issued in PCT/JP2014/083358 dated Mar. 10, 2015 (2 pages).
(Continued)

*Primary Examiner* — Steven J Ganey
(74) *Attorney, Agent, or Firm* — Osha Liang LLP

(57) ABSTRACT

A jet stream generating device that generates a jet stream of liquid includes: a cylindrical liquid chamber; a nozzle configured to open an end part of the liquid chamber and inject liquid F in the liquid chamber to outside; a liquid supply path configured to supply liquid F into the liquid chamber; a laser beam irradiation part configured to irradiate a pulse laser beam into the liquid chamber, and vaporize the liquid F in the liquid chamber; and a laser oscillator configured to control laser beam intensity and laser beam pulse width independently. An inner surface of the liquid chamber has a mirror plane for reflecting and guiding the pulse laser beam emitted from the laser beam irradiation part to the end part of the liquid chamber, and an adjusting part configured to
(Continued)

adjust a distance between the nozzle and the laser beam irradiation part is included.

3 Claims, 12 Drawing Sheets

(51) Int. Cl.
*A61B 17/295* (2006.01)
*A61B 1/00* (2006.01)
*A61B 1/015* (2006.01)
*B05B 7/16* (2006.01)
*B05B 9/00* (2006.01)
*B05B 7/24* (2006.01)
*B05B 12/06* (2006.01)

(52) U.S. Cl.
CPC .............. *A61B 17/295* (2013.01); *B05B 7/16* (2013.01); *B05B 7/2408* (2013.01); *B05B 9/002* (2013.01); *B05B 12/06* (2013.01); *A61B 2217/005* (2013.01)

(58) Field of Classification Search
USPC ........ 239/101, 128, 135, 302, 589, 1; 606/7, 606/14, 15, 16, 19, 167; 604/19, 20, 22
See application file for complete search history.

(56) References Cited

U.S. PATENT DOCUMENTS

| | | |
|---|---|---|
| 2003/0139041 A1 | 7/2003 | LeClair |
| 2005/0124985 A1 | 6/2005 | Takayama et al. |
| 2006/0247743 A1 | 11/2006 | Hayakawa et al. |
| 2012/0232341 A1 | 9/2012 | Seto et al. |

FOREIGN PATENT DOCUMENTS

| | | |
|---|---|---|
| JP | 2007-209465 A | 8/2007 |
| JP | 2008-017865 A | 1/2008 |
| JP | 2012-187291 A | 10/2012 |

OTHER PUBLICATIONS

Written Opinion of the International Searching Authority issued in PCT/JP2014/083358 dated Mar. 10, 2015 (6 pages).

Extended European Search Report in counterpart European Application No. 14 88 2998.9 dated Sep. 7, 2017 (5 pages).

* cited by examiner

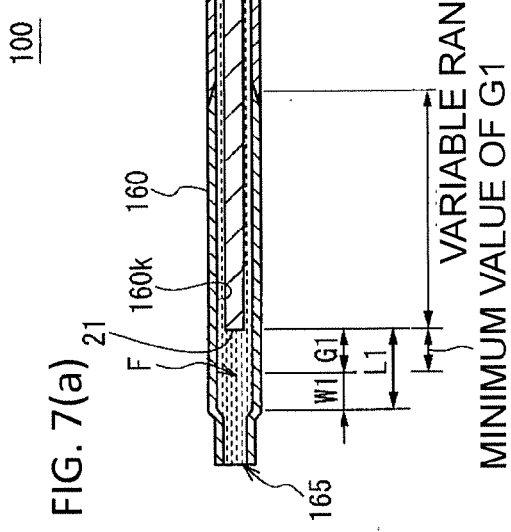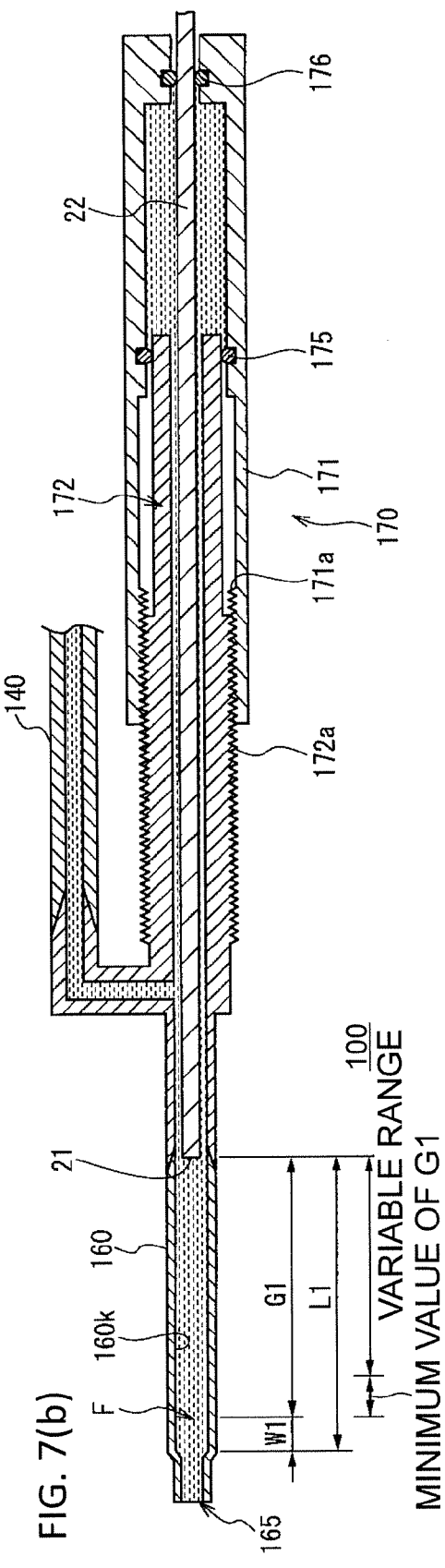

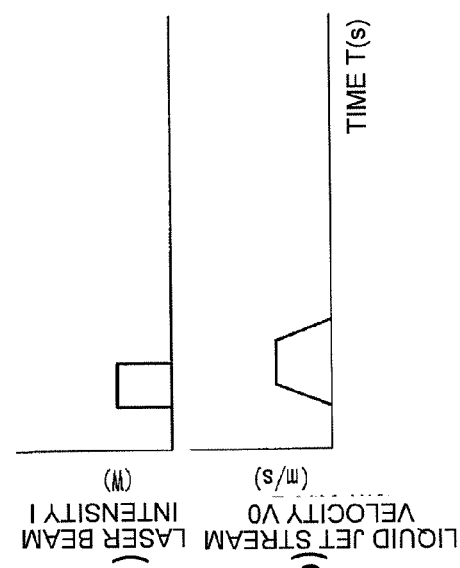
FIG. 8(a) LASER BEAM INTENSITY I (W)
FIG. 8(b) LIQUID JET STREAM VELOCITY V0 (m/s)
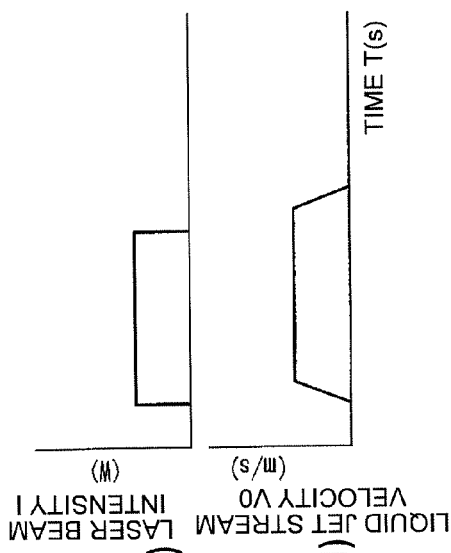
FIG. 8(c) LASER BEAM INTENSITY I (W)
FIG. 8(d) LIQUID JET STREAM VELOCITY V0 (m/s)
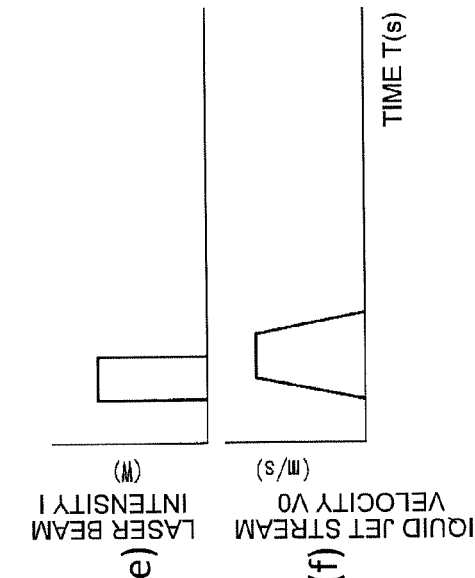
FIG. 8(e) LASER BEAM INTENSITY I (W)
FIG. 8(f) LIQUID JET STREAM VELOCITY V0 (m/s)
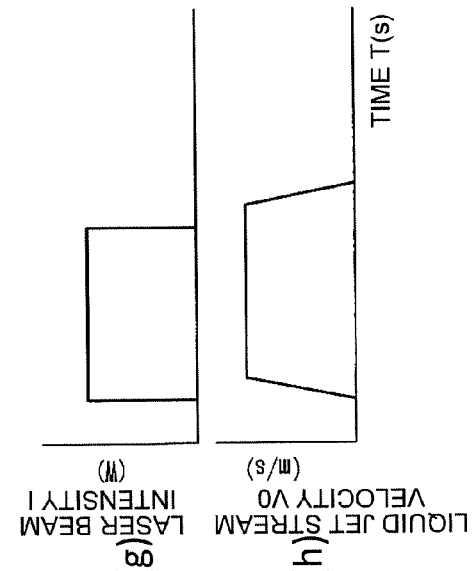
FIG. 8(g) LASER BEAM INTENSITY I (W)
FIG. 8(h) LIQUID JET STREAM VELOCITY V0 (m/s)

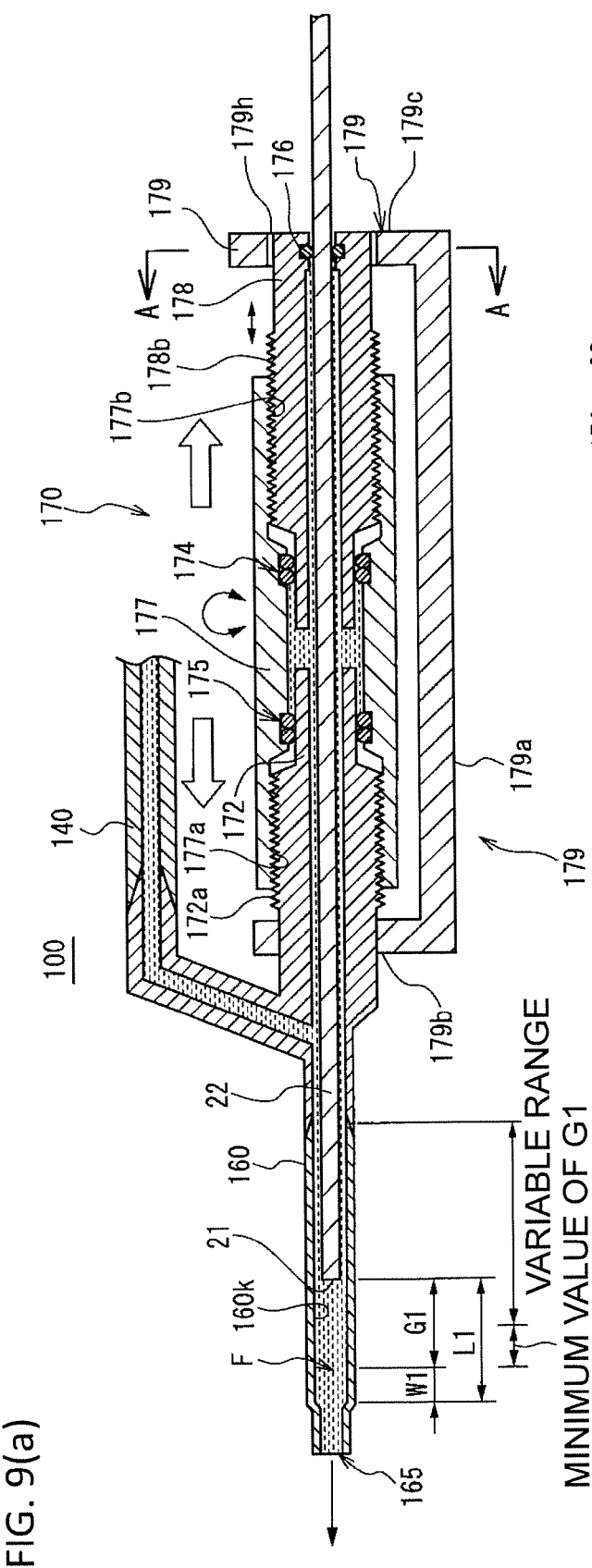
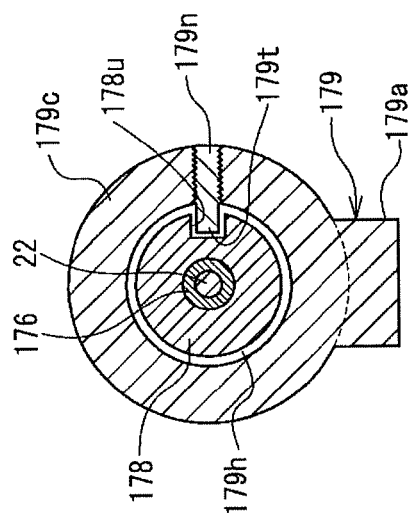
FIG. 9(a)
FIG. 9(b)

JET STREAM GENERATING DEVICE AND JET STREAM GENERATING METHOD

BACKGROUND OF THE INVENTION

Field of the Invention

The present invention relates to a jet stream generating device, and a jet stream generating method of the jet stream generating device.

Description of the Related Art

A jet knife to cut and crush biotissue using a liquid jet stream has been turned into practical use. A jet knife using a high-pressure pump is also known. The jet knife is a surgical device in which liquid boosted by a high-pressure pump is injected from a jet nozzle to acquire a continuous jet stream, this jet stream is irradiated onto biotissue, and a cutting and crushing effects are acquired by the kinetic energy thereof.

These effects of the jet knife are acquired at low temperature (e.g. room temperature) since thermal energy is not used, unlike a laser knife or a high frequency knife. Further, unlike the case of an ultrasonic knife of which active part is solid metal, in the case of the jet knife of which the active part is liquid, liquid itself transforms after collision with biotissue and applies pressure to the biotissue, and acts on a segment of the biotissue that has low elasticity, that is, the jet knife acts on biotissues having different elastic characteristics differently. This characteristic of the jet knife allows to cut and crush biotissue differently using uniform jet irradiation, thus preserving a specific segment.

In medical fields, it is demanded to develop a surgical instrument that can simply select and cut only an arbitrary segment or an affected portion in a biotissue where many segments coexist in a tangled web of tissue, and a jet knife using a liquid jet stream, which can determine crushing or preserving a biotissue utilizing the difference of elastic characteristics of the biotissue, is highly expected as a surgical instrument.

A jet knife using a high pressure pump can only coarsely adjust the output of the jet stream by adjusting the output of the high-pressure pump, therefore this jet knife is inappropriate for surgery to remove a thrombosis or the like, utilizing a subtle difference of the elastic characteristics in biotissue. Further, if a jet stream is continuously irradiated onto a living body, and if the jet stream infiltrates into the vascular system, pressure waves of the stream propagate inside the vessels at sonic speed, damaging a segment that is sensitive to pressure. A vascular network is formed in a living body, so the pressure waves may propagate in a wide range and even damage a segment in a distant location.

A surgical instrument (pulse jet knife) is known, where an optical fiber is inserted into a tube, liquid such as water, that is filled into a tube, is rapidly heated by a laser beam emitted from a laser oscillator via the optical fiber to generate a liquid jet stream, and a thrombosis or the like is crushed and removed by the force of the liquid jet stream.

A laser-induced liquid jet stream generating device according to Patent Literature 1 has a jet generating tube part, which encloses a laser irradiation part formed in a tip part of the optical fiber, and generates a jet stream. This laser-induced liquid jet stream generating device has a Y connector and a connecting member that connects the Y connector to a laser oscillator, the connecting member includes a connecting protrusion that protrudes from the laser oscillator, and a sleeve member which is screwed to the connecting protrusion, so that the laser oscillator and the Y connector can be detachably connected. The optical fiber penetrates through a predetermined port of the Y connector, and the optical fiber is fixed to the sleeve member by a fixing material, such as resin. In other words, the laser irradiation part formed in the tip part of the optical fiber is fixed to a predetermined position inside the jet generating tube part.

Now a principle of generating a jet stream by the jet stream generating device will be described in brief. Here a jet stream generating device (expansion chamber length-fixed type) in which the optical fiber is fixed at a predetermined position in the liquid chamber, in other words, in which the length of the expansion chamber is fixed, will be described.

For example, in the case of a jet stream generating device 100B shown in FIG. 10(a), an inner surface of a cylindrical liquid chamber B160 is formed as a rough surface B160r. If the pulse laser beam is irradiated from a laser beam irradiation part 21 at the tip part of an optical fiber 22 onto a liquid F inside the liquid chamber B160, the liquid F in the neighboring region of the tip part is heated, a bubble G is generated in the neighboring region of the tip part as shown in FIG. 10(b), and the liquid F is pushed out from a nozzle B165. If the laser beam is continuously irradiated, the bubble G expands as shown in FIG. 10(c), and the liquid F is injected from the nozzle B165. Among the lights emitted from the laser beam irradiation part 21 at the tip part of the optical fiber 22, the light irradiated onto the rough surface B160r of the inner surface of the liquid chamber B160 is easily scattered or absorbed by the rough surface B160r. The energy of the laser beam to reach a boundary surface FG of the bubble G is small.

For example, the absorption coefficient of the laser beam, of which wavelength λ is 2100 nm in water, is about 50 cm$^{-1}$. This means that when the laser beam travels 1 mm in water, 99.3% of the energy of the light is absorbed by the water.

The absorption of the laser beam by water is based on the vibrational level of water molecules, and the absorptivity is in proportion to the molecular density. Water at 100° C. phase-changes into vapor, of which volume is about 1700 times that of water by vaporization. Because of the phase-change from liquid into vapor, the molecular density drops to about 1/1700. This means that for 99.3% of the energy of the light to be absorbed by the vapor, about a 1700 mm optical path length is required in the vapor.

A concrete example will be described. When an optical fiber, of which numerical aperture NA is 0.22 and core diameter is 0.4 mm, is installed in a thin tube of which inner diameter is 1 mm, and a laser beam is emitted from the tip of the optical fiber, the ratio of the light emitted from the opening of the thin tube, with respect to the incident energy, was calculated with a distance D1 from the optical fiber emit end (tip) to the nozzle side as a variable, assuming that the inner surface of the thin tube is a scattering absorber (e.g. rough surface) (see FIG. 11). In FIG. 11, the ordinate indicates the transmittance, and the abscissa indicates the distance D1 from the optical fiber emit end (tip). As shown in FIG. 11, about 91.5% of the light energy is lost at the D1=10 mm position.

The maximum length of the expanded gas (vapor) inside the thin tube (liquid chamber 160 (B160)), of which inner surface the scattering absorber (rough surface) is formed on, will be described (see FIG. 12). According to an experiment using a high-speed camera, if a pulse laser beam, of which pulse width T1 is 300 μs and pulse energy E0 is 1 J, is transmitted via an optical fiber 22, of which numerical aperture NA is 0.22 and core diameter is 0.4 mm, and the pulse laser beam is emitted from the laser beam irradiation part at the tip part of the optical fiber 22 through the thin tube (1 mm inner diameter) filled with water (liquid F), the maximum value of the length G1 of the expanded gas (vapor bubble G) generated inside the thin tube (length in the tube axis direction) is about 20 mm.

In other words, in the case of using the thin tube, of which inner surface the rough surface is formed on, as the liquid chamber B160, a maximum 20 mm long expanded gas (bubble G) is generated because of the loss of the light energy, and the liquid F is injected from the opening-shaped nozzle 165 (B165) which opens at the end part 160a of the liquid chamber B160.

A catheter according to Patent Literature 2 includes a reinforcing member constituted by a material, which has a high melting point to withstand the heat generated by the optical fiber and predetermined rigidity, on the inner surface of the tube near the laser beam irradiation position.

A laser-induced liquid jet stream generating device according to Patent Literature 3 has a jet generating tube part in which an optical fiber is inserted, and this jet generating tube part is constituted by such a material as gold, platinum, silver, copper, aluminum or an alloy thereof (e.g. 18 K gold, platiniridium) so as to withstand the laser beam and the heat induced by the laser beam.

CITATION LIST

Patent Literature

[Patent Literature 1] Japanese Published Patent Application No. 2007-209465
[Patent Literature 2] Japanese Published Patent Application No. 2005-152094
[Patent Literature 3] Japanese Published Patent Application No. 2008-17865

SUMMARY

To increase the intensity and duration of the liquid jet, the maximum value of the length G1 of the expanded gas (bubble G) shown in FIG. 12 must be increased.

However, even if the pulse width and pulse energy of the laser beam are increased, the maximum value of the length G1 of the expanded gas (bubble G) increases very little. To be more specific, the light emitted from the tip part of the optical fiber 22 is easily scattered and absorbed by the rough surface on the inner surface of the liquid chamber B160, hence the intensity of the light reflected by the rough surface is low. The energy of the light that reaches the boundary surface FG between the liquid F and the bubble G (gas) from the tip part of the optical fiber 22 decreases as the distance between the tip part of the optical fiber and the boundary surface FG increases.

The jet stream is generated by vaporizing expansion due to the liquid F absorbing the pulse laser beam, and the volume of the expanded gas (bubble G) increases due to the increase in the injected pulse energy and expansion of the pulse width, where if the liquid chamber B160 has a thin diameter cylindrical shape, for example, the distance between the tip part of the optical fiber 22 and the boundary surface FG (gas-liquid interface) increases, and the injected laser beam cannot be efficiently absorbed by the liquid F. In other words, in the state where the distance between the gas-liquid interface and the tip part of the optical fiber 22 is short (in the state where the gas-liquid interface and tip part of the optical fiber 22 are close to each other), the injected laser beam is directly irradiated onto the gas-liquid interface and absorbed, but as the distance between the gas-liquid interface and the tip part of the optical fiber 22 increases, the laser beam emitted from the tip part of the optical fiber 22 is irradiated onto the inner surface of the liquid chamber B160 and attenuates through the scattering and absorption. Since the light energy amount causing vaporization of the liquid F drops, the intensity of the jet stream drops.

In other words, as the bubble G generated in the liquid chamber B160 becomes larger, the volume expansion velocity of the bubble G decreases, and the jet stream velocity of the liquid F injected from the nozzle B165 does not exceed a predetermined value. As the bubble G becomes larger, the jet stream generation efficiency of the liquid F drops.

The catheter according to Patent Literature 2 includes the reinforcing member constituted by a material, which has a high melting point to withstand the heat generated by the optical fiber and a predetermined rigidity, on the inner surface of the tube near the laser beam irradiation position, but this reinforcing member does not contribute to increasing the maximum value of the length of the expanded gas (bubble).

The laser-induced liquid jet stream generating device according to Patent Literature 3 has a jet generating tube part in which an optical fiber is inserted, and this jet generating tube part is constituted by a material that withstands the laser beam and heat induced by the laser beam when irradiating the laser inside the jet generating tube part, but this jet generating tube part does not contribute to increasing the maximum value of the length of the expanded gas (bubble).

In the example shown in FIG. 12, in order to increase the pulse width of the jet stream outputted from the nozzle, the distance L1 from the optical fiber emit end to the nozzle must meet condition A in terms of the safety required for the liquid jet knife, that is, $L1 > G1$ so that the expanded gas (bubble G) having a high temperature and high pressure is not injected from the nozzle.

Further, the distance L1 from the optical fiber emit end and the nozzle must meet condition B, that is, $W1 = L1 - G1$ must be very small. W1 is a value generated by subtracting the length G1 of the expanded gas (bubble G) from the distance L1 from the optical fiber emit end to the nozzle when the expanded gas (bubble G) is generated, and is a length of the liquid that remains in the tube near the nozzle. If W1 is large, the fluid resistance caused by the movement of the liquid F increases and the energy of the liquid jet is lost, hence W1 must be a small value, such as 10 mm.

In order to make the pulse energy E0 and the pulse width T1 variable under the laser irradiation conditions, while satisfying the above mentioned condition A and condition B, the distance L1 is required to be variable.

However, in the case of the laser-induced liquid jet stream generating device according to Patent Literature 1, for example, the optical fiber is fixed to the Y connector and the laser irradiation part formed in the tip part of the optical fiber is fixed to a predetermined position inside the jet generating tube part, and there is no structure to make the distance L1 variable.

In the case of a general purpose pulse jet knife (surgical instrument), only the output values related to the laser, such as the pulse width of the laser beam and the adjustment of the pulse energy, are set to predetermined values, and a specific jet stream output value and jet stream output time are fixed, therefore this general purpose pulse jet knife can be used only for a single purpose, such as removing a specific biotissue.

To distinguish between the crushing and preserving of biotissue, surgery must be performed keeping the biotissue to be preserved in a stable state. In actual surgery, it is difficult to accurately predict the specifics of the elastic differences between biotissues based on individual differences and segmental differences (e.g. difference of organ, position of organ), and the elastic differences between biotissues based on the pathological progression of an affected segment. In the case of a general purpose pulse jet knife, it is difficult to finely adjust the jet stream output, so the actual use of the pulse jet knife is only for a segment where elastic differences are obvious. Further, it is difficult to precisely predict the elastic differences between biotissues generated by pathological progression of the affected segment, therefore a conventional pulse jet knife is unsuitable for use in surgery where there is zero tolerance for error.

Furthermore, in the case of a general purpose pulse jet knife (surgical instrument), to crush an affected segment, the knife must be used for several short periods of time under a same level of cutting ability.

The crushing force (impulsive force) of the jet stream of the pulse jet knife is an impulse of the force that acts on the biotissue during a very short time. If the sectional area of the nozzle (the sectional area of the liquid jet stream) is assumed to be constant, the velocity (initial velocity) of the jet stream is in proportion to the force that acts on the biotissue. Therefore the product of the velocity (initial velocity) of the jet stream and the duration is in proportion to the impulse, and the crushing force is in proportion to the product of the velocity (initial velocity) of the liquid jet stream and the duration. When the jet stream of this pulse jet knife acts on biotissue, damage to biotissue to be preserved may accumulate.

Therefore, a surgical instrument that can minimize damage to biotissue to be preserved is demanded. More specifically, a surgical instrument, which can finely control the crushing force of the jet stream by adjusting not only the velocity (initial velocity) of the jet stream but also the duration of the jet stream, is demanded.

One or more embodiments of the invention provide a jet stream generating device that generates a jet stream having high velocity; to provide a jet stream generating device having a simple configuration that allows generating a jet stream of liquid at high efficiency; a jet stream generating device that allows making the flow rate and energy of the jet stream variable using a simple configuration; a jet stream generating device that allows easily controlling the jet stream time using a simple configuration; a jet stream generating device used as surgical device to limit the propagation range of the pressure wave in a living body by generating the jet stream intermittently; a jet stream generating device that allows operating with finely distinguishing the crushing region from the preserving region, by finely controlling the differentiation of the cutting and crushing effect by the liquid jet stream utilizing the elastic differences of biotissues; and a jet stream generating method of the jet stream generating device; among others.

A jet stream generating device according to one or more embodiments of the present invention includes at least the following configuration.

A jet stream generating device configured to generate a jet stream of liquid, having:

a cylindrical liquid chamber;
a nozzle configured to open an end part of the liquid chamber and inject liquid in the liquid chamber to outside;
a liquid supply path configured to supply liquid into the liquid chamber;
a laser beam irradiation part configured to irradiate a pulse laser beam into the liquid chamber, and vaporize the liquid in the liquid chamber; and
a laser oscillator configured to control laser beam intensity and laser beam pulse width independently, wherein
an inner surface of the liquid chamber has a mirror plane for reflecting and guiding the pulse laser beam emitted from the laser beam irradiation part to the end part, and
an adjuster configured to adjust a distance between the nozzle and the laser beam irradiation part is included.

A jet stream generating method of a jet stream generating device according to one or more embodiments of the present invention includes at least the following configuration.

A jet stream generating method of a jet stream generating device configured to generate a jet stream of liquid, wherein
the jet stream generating device includes
a cylindrical liquid chamber;
a nozzle configured to open an end part of the liquid chamber and inject liquid in the liquid chamber to outside;
a liquid supply path configured to supply liquid into the liquid chamber;
a laser beam irradiation part configured to irradiate a pulse laser beam into the liquid chamber, and vaporize the liquid in the liquid chamber; and
a laser oscillator configured to control laser beam intensity and laser beam pulse width independently,
an inner surface of the liquid chamber has a mirror plane for reflecting and guiding the pulse laser beam emitted from the laser beam irradiation part to the end part, and
an adjuster configured to adjust the distance between the nozzle and the laser beam irradiation part is included,
comprising the step of
adjusting by the adjuster a distance between the nozzle and the laser beam irradiation part before or at the irradiation of the pulse laser beam by the laser beam irradiation part.

According to one or more embodiments of the present invention, a jet stream generating device that generates a jet stream having high velocity can be provided with a simple configuration.

Further, according to one or more embodiments of the present invention, a jet stream generating device that generates a jet stream of liquid at high efficiency can be provided with a simple configuration.

Further, according to one or more embodiments of the present invention, a jet stream generating device that allows to make the flow rate and energy of the jet stream variable can be provided with a simple configuration.

Further, according to one or more embodiments of the present invention, a jet stream generating device that allows to easily adjust the jet stream time can be provided with a simple configuration.

Further, according to one or more embodiments of the present invention, when the jet stream generating device is used as a surgical device, the propagation range of the pressure wave in a living body can be limited by generating the jet stream intermittently, which improves safety.

Further, according to one or more embodiments of the present invention, when the jet stream generating device is used as a surgical device, a jet stream generating device that allows operating with finely distinguishing the crushing region from the preserving region, by finely controlling the differentiation of the cutting and crushing effect by the liquid jet stream utilizing the elastic differences of biotissues, and allows to cut, crush or preserve complicated forms of biotissues without depending on the skill of surgeon, can be provided.

Further, according to one or more embodiments of the present invention, a jet stream generating method of the jet stream generating device can be provided.

BRIEF DESCRIPTION OF THE DRAWINGS

FIG. 7(a) is a diagram depicting an example of the operation of the adjusting part of the jet stream generating device shown in FIG. 6 in the state when the tip part of the optical fiber moved to the nozzle side;

FIG. 7(b) is a diagram depicting an example of the operation of the adjusting part of the jet stream generating device shown in FIG. 6 in the state when the tip part of the optical fiber moved to the opposite side of the nozzle;

FIGS. 8(a) and 8(b) are diagrams each depicting an example of the time-based changes of the laser beam intensity and the liquid jet stream velocity when a jet stream is generated at low jet stream velocity for a short duration according to one or more embodiments of the invention;

FIGS. 8(c) and 8(d) are diagrams each depicting an example of the time-based changes of the laser beam intensity and the liquid jet stream velocity when a jet stream is generated at low jet stream velocity for a long duration according to one or more embodiments of the invention;

FIGS. 8(e) and 8(f) are diagrams each depicting an example of the time-based changes of the laser beam intensity and the liquid jet stream velocity when a jet stream is generated at high jet stream velocity for a short duration according to one or more embodiments of the invention;

FIGS. 8(g) and 8(h) are diagrams each depicting an example of the time-based changes of the laser beam intensity and the liquid jet stream velocity when a jet stream is generated at high jet stream velocity for a long duration according to one or more embodiments of the invention;

FIG. 9(a) is a diagram depicting a lateral cross-sectional view of a jet stream generating device which includes a rotation stopping member according to one or more embodiments of the invention;

FIG. 9(b) is a diagram depicting an across-sectional view along the A-A line shown in FIG. 9(a);

DETAILED DESCRIPTION

Figure 1:
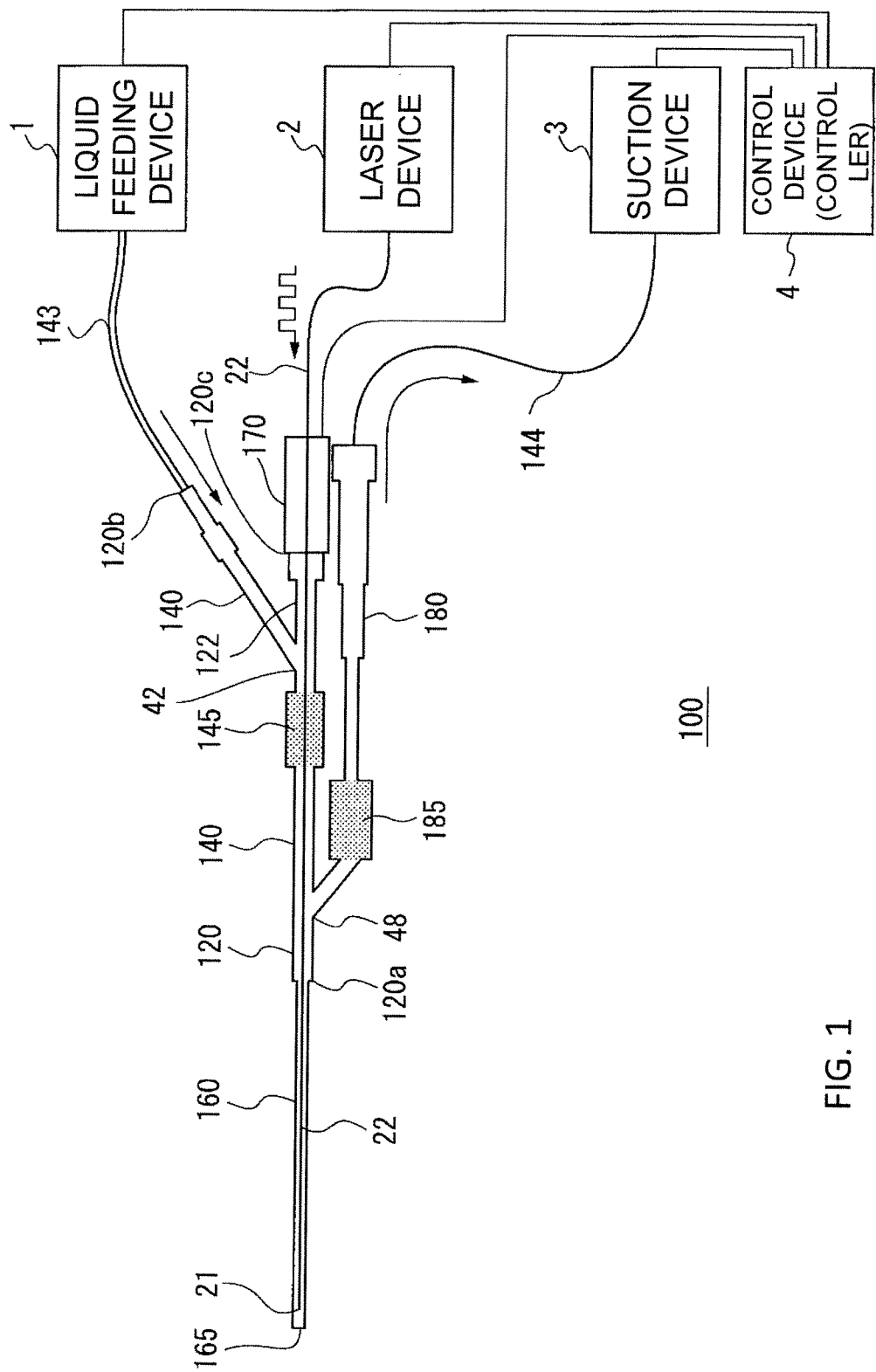
FIG. 1 is a diagram depicting a general configuration of an example of a jet stream generating device according to one or more embodiments of the present invention.

An overview of one or more embodiments of the present invention will be described.

A jet stream generating device according to one or more embodiments of the present invention heats liquid in a liquid chamber (expansion chamber) by a pulse laser beam to induce vaporization and expansion, and intermittently generates a liquid jet stream (pulse jet) utilizing the vaporizing expansion pressure.

The cutting and crushing effect of the pulse jet on a biotissue is in proportion to the product of the force acting on the biotissue and the acting time T0. Therefore in order to finely control the crushing effect by the pulse jet, the impulsive force F0 and the time T0 must be finely controlled.

The impulsive force F0 that is generated when a pulse jet, which was injected under the conditions of cross-section S, length L, density ρ and velocity V0, collides with the biotissue, is the same as the change amount of the momentum of the liquid that collides in a unit time, if the effect caused by the change of the shape of the liquid is ignored (see Expression (1)).

$$F0 = S * L * \rho * V0 \tag{1}$$

If the cross-section of the jet nozzle is constant, the density ρ is constant, hence the impulsive force F0 depends on the velocity V0.

This means that to finely control the crushing effect, the force that acts on the biotissue and the time should be controlled, and to be more specific, the initial velocity and acting time should be independently controlled. To finely control the crushing effect, it is more advantageous to control the initial velocity and acting time using two independent parameters.

In order to independently control V0 (initial velocity) and T0 (duration of jet stream), the output P0 of the laser, which is the heating source, and the pulse width T1 of the laser should be controlled.

However, if the transfer efficiency of the laser beam to the liquid changes due to the form of the liquid chamber (expansion chamber), V0, T0/P0 and T1 do not act linearly. A change in the transfer efficiency is caused when the laser beam emitted from the optical fiber is absorbed by the inner surface of the expansion chamber before reaching the liquid.

Furthermore, if P0 or T1 is high, there is danger that the expanded high temperature vaporized gas may be injected from the nozzle, hence the laser beam emitting part of the optical fiber must be moved away from the nozzle, in order to expand the volume of the expansion chamber.

In the jet stream generating device according to an embodiment of the present invention, V0 and T0 are made variable by making P0 and T1 variable, and the interval between the emitting part of the laser beam of the optical fiber and the nozzle is made variable so as to finely control the crushing effect, and moreover, the inner surface of the liquid chamber (expansion chamber) has a reflection structure so that the absorption of the laser beam by the inner surface can be suppressed.

One or more embodiments of the present invention will now be described with reference to the drawings.

One or more embodiments of the present invention include the content of the drawings, but the present invention is not limited to this. In the following description on each drawing, a portion common to the already described portion is denoted with the same sign, and redundant description is partially omitted.

Figure 2:
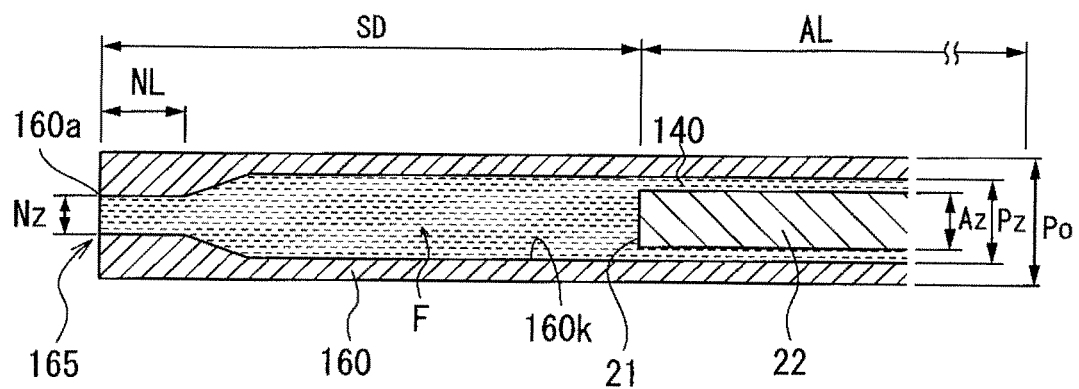
FIG. 2 is a partially enlarged view of an area near a tip part of a cylindrical liquid chamber (pipe) of the jet stream generating device according to one or more embodiments of the present invention.

FIG. 1 is a diagram depicting a general configuration of a jet stream generating device 100 according to one of more embodiments of the present invention. FIG. 2 is a partially enlarged view of an area near a tip part of a cylindrical liquid chamber 160 of the jet stream generating device. An example of applying the jet stream generating device 100 according to one or more embodiments of the present invention to a water jet knife used as a medical instrument will be described. The jet stream generating device 100, according to one or more embodiments of the present invention, may be called a "pulse laser heating jet stream generating device", which has a laser-induced liquid jet stream generating device and an expansion chamber (liquid chamber) having a wave guide tube structure.

The jet stream generating device 100 has a Y connector 120, a liquid supply path 140 (fluid supply path), and the cylindrical liquid chamber 160 (thin metal tube or the like). The jet stream generating device 100 also has a liquid feeding device 1, a laser device 2 (laser oscillator), a suction device 3, and a control device 4 (controller).

The Y connector 120 is a holding member held by a surgeon. The Y connector 120 has approximately a Y-shaped cylindrical body, and has a first end part 120a, a second end part 120b and a third end part 120c. The first end part 120a has a thin metal tube, which is the cylindrical liquid chamber 160. The liquid feeding device 1 is connected to the second end part 120b via a tubular member 143 such as a tube. A filter 145, for removing impurities in the liquid, is installed in the liquid supply path 140. The laser device 2 is connected to the third end part 120c via an optical fiber 22. In this embodiment, an adjusting part 170 (adjuster) is installed in the third end part 120c. The optical fiber 22 is inserted into the Y connector 120 through the adjusting part 170 which is installed in the third end part 120c of the optical fiber path 122 of the Y connector 120, and the tip of the optical fiber 22 is disposed in a predetermined position inside the thin metal tube, which is the cylindrical liquid chamber 160. The adjusting part 170 can adjust the positions of the Y connector 120 and the tip part of the optical fiber 22 inserted into the liquid chamber 160. Specifically, the adjusting part 170 is configured to adjust the distance between the laser beam irradiation part 21, which is disposed in the tip part of the optical fiber 22, and the nozzle 165, as mentioned later.

In this embodiment, a part of the Y connector 120 has a structure that can serve as both a liquid supply path 140 and an optical fiber path 122.

In this embodiment, a suction passage 180 is disposed in the Y connector 120, and the suction device 3 is disposed in the suction passage 180 via a tubular member 144, such as a tube. A filter 185 configured to remove impurities in the liquid F is disposed in the suction passage 180.

In this embodiment, the Y connector 120 is configured such that a connecting position 48 of the liquid supply path 140 and the suction passage 180 is located between a connecting position 42 of the liquid supply path 140 and the optical fiber path 122, and the first end part 120a.

The liquid feeding device 1 supplies liquid to the cylindrical liquid chamber 160, such as a metal cylindrical member, via the liquid supply path 140, based on the control of the control device 4 (controller). The liquid F in the liquid chamber 160 is, for example, water, saline solution and electrolytes.

The laser device 2 (laser oscillator) generates the pulse laser beam based on the control of the control device 4 (controller). The pulse laser beam outputted from the laser device 2 is emitted from the laser beam irradiation part 21 at the tip part of the optical fiber 22 to the cylindrical liquid chamber 160 via the optical fiber 22. The laser device 2 (laser oscillator) can independently control the laser beam intensity and the laser beam pulse width. Specifically, the control device 4 (controller) controls the laser device 2 so as to change the pulse energy, pulse width and pulse repeat frequency of the pulse laser beam irradiated by the laser beam irradiation part 21. The laser device 2 that is used in this embodiment can irradiate a pulse laser beam having about a maximum 1000 mJ pulse energy per pulse.

In this embodiment, for the laser device 2, a laser oscillator, such as a holmium YAG laser device (Ho:YAG laser: 2.1 μm wavelength), can be used. The liquid F, such as water, saline solution and electrolytes, absorbs the energy of the pulse laser beam of the Ho:YAG laser or the like. The laser device 2, however, is not limited to the above mentioned laser oscillator.

The suction device 3 is connected to the Y connector 120 via the tubular member 144, such as a tube, and is configured to suck the liquid in the cylindrical liquid chamber 160 when necessary, based on the control of the control device 4 (controller).

The control device 4 (controller) systematically controls various devices, including the liquid feeding device 1, the laser device 2 and the suction device 3. The control device 4 is constituted by a computer or the like, and implements the functions related to the control according to one or more embodiments of the present invention, by executing control programs stored in a memory and a storage device. Further, the control device 4 (controller) variably controls one or a combination or all of: the amount of the jet stream, the flow rate of the jet stream and the repeat frequency of the jet stream, by changing the pulse energy, the pulse width and the pulse repeat frequency of the pulse laser beam irradiated by the laser beam irradiation part 21.

Furthermore, the control device 4 (controller) performs a treatment to adjust the distance between the laser beam irradiation part 21, which is disposed in the tip part of the optical fiber 22, and the nozzle, by controlling the adjusting part 170 (adjuster). In concrete terms, the adjusting part 170 may have a driving device, such as a motor, and the control device 4 may perform the treatment to adjust the distance between the laser beam irradiation part 21 and the nozzle, by driving the driving device of the adjusting part 170. In this case, the control device 4 (controller) performs the treatment to adjust the distance between the laser beam irradiation part 21 and the nozzle using the adjusting part 170, according to the pulse width, the pulse energy, the pulse repeat frequency and the like of the pulse laser beam emitted from the laser beam irradiation part 21. This control device 4 may perform the above mentioned treatment based on the setting information stored in the storage part. Further, a detection part for detecting the flow rate, the energy or the like of the jet stream outputted from the nozzle may be disposed, so that the control device 4 performs the control of the adjusting part 170 based on the detection signal from the detection part.

In the example shown in FIG. 2, the liquid chamber 160 is formed in a cylindrical shape. In this embodiment, the liquid chamber 160 is formed in a circular cylindrical shape. Specifically, the liquid chamber 160 is formed in a circular cylindrical shape of which outer diameter is Po and the inner diameter is Pz. The cylindrical liquid chamber 160 is constituted by a material having high strength, such as a metal material. The material constituting the liquid chamber 160 can be, for example, such metals as stainless steel, titanium, gold and silver, or ceramics. In this embodiment, the liquid chamber 160 is a thin metal tube of which inner diameter Pz is about 0.5 mm to 3.0 mm. An example of the inner diameter Pz is about 1.0 mm.

An opening-shaped nozzle 165 is disposed in the end part 160a of the liquid chamber 160. The nozzle 165 is configured to inject the liquid F inside the liquid chamber 160 to the outside. In this embodiment, the diameter Nz of the nozzle 165 is smaller than the inner diameter Pz of the cylindrical liquid chamber 160, as shown in FIG. 2. The length NL in the axis direction of the nozzle 165, of which diameter is Nz, is shorter than the distance SD between the end part 160a of the liquid chamber 160, in which the nozzle 165 is disposed, and the tip of the optical fiber 22. In this embodiment, the distance SD between the end part 160a of the liquid chamber 160 and the tip of the optical fiber 22 is about 50 mm to 150 mm. An example of the distance is about 100 mm. This distance SD is set to a distance with which the bubble, which is generated and expanded inside the liquid chamber 160 by the laser beam irradiation, does not protrude out of the nozzle 165 disposed in the end part 160a of the liquid chamber 160.

As shown in FIG. 2, the optical fiber 22 is inserted into the cylindrical liquid chamber 160 from the opposite side of the nozzle 165. The length AL of the optical fiber 22 inside the cylindrical liquid chamber 160 is configured to be adjustable. The tip part of the optical fiber 22 functions as the laser beam irradiation part 21. The liquid F inside the liquid chamber 160 absorbs the energy of the laser beam irradiated from the laser beam irradiation part 21. The laser beam irradiation part 21 irradiates the pulse laser beam into the liquid chamber 160, and heats and vaporizes the liquid F inside the liquid chamber 160.

The diameter Az of the optical fiber 22 is smaller than the inner diameter Pz of the cylindrical liquid chamber 160. A gap is created between the optical fiber 22 and the inner surface of the cylindrical liquid chamber 160, and this gap functions as the liquid supply path 140. To be more precise, this liquid supply path 140 supplies the liquid F into the liquid chamber 160 (in a space between the nozzle 165 and the laser beam irradiation part 21, which is a tip part of the optical fiber 22).

The inner surface of the cylindrical liquid chamber 160 has a mirror plane 160k which reflects the pulse laser beam emitted from the laser beam irradiation part 21, and guides the pulse laser beam to the end part 160a of the liquid chamber 160 or the nozzle 165 which is formed in the end part 160a. In other words, the energy loss of the laser beam becomes very small if the laser beam is reflected by the mirror plane 160k. Therefore, the pulse laser beam emitted from the laser beam irradiation part 21 can be reflected by the mirror plane 160k on the inner surface of the cylindrical liquid chamber 160 once or a plurality of times, and be irradiated onto the boundary surface (gas-liquid interface) of the bubble. The boundary surface (gas-liquid interface) between the liquid F and the bubble here refers to the boundary surface (gas-liquid interface) of the bubble inside the cylindrical liquid chamber 160 on the opening side (nozzle 165 side) of the cylindrical liquid chamber 160.

In one or more embodiments of the invention, this mirror plane 160k is formed on the area near the laser beam irradiation part 21 at the tip part of the optical fiber 22, on the inner surface of the cylindrical liquid chamber 160, and on all or a part of the area from the part near the laser beam irradiation part 21 to the nozzle 165.

The mirror plane 160k is a surface treated by one of: an electrolytic polishing treatment, a reaming treatment, a plating treatment, a vapor deposition treatment and an abrasive blowing treatment. Specifically, if a thin metal tube made of stainless steel, titanium or the like is used for the cylindrical liquid chamber 160, the mirror plane 160k may be formed by optically polishing the inner surface thereof. The mirror plane 160k may be formed by coating with a material of which reflectance is high with respect to the laser wavelength of the pulse laser beam. Specifically, a gold coating, a gold plate coating or the like may be performed to form the mirror plane 160k. Further, in the cylindrical liquid chamber 160, the mirror plane 160k may be formed by press-fitting a thin tube (gold), which has a thin thickness and high reflectance, into a thin metal tube made of stainless, titanium or the like. For the abrasive blowing treatment, a treatment of blowing micro-particles, on which abrasive is adhered (e.g. micro-resin particles) into the cylindrical liquid chamber 160 at high-speed, can be used.

In one or more embodiments of the invention, the mirror plane 160k on the inner surface of the liquid chamber 160 has a predetermined value or higher reflectance with respect to the pulse laser beam irradiated by the laser beam irradiation part 21.

<Operation of Jet Stream Generating Device 100>

FIG. 3 is a set of diagrams depicting an example of the operation of the jet stream generating device according to one or more embodiments of the present invention. FIG. 3(a) is a state before the pulse laser beam irradiation, FIG. 3(b) is an initial state of the pulse laser beam irradiation (initial state of bubble generation), FIG. 3(c) is a state when the pulse laser beam is irradiated and the bubble is expanded, and FIG. 3(d) is a state when the pulse laser beam is not irradiated. FIG. 4 is a set of diagrams depicting examples of the pulse laser beam intensity generated by the jet stream generating device and the initial velocity of the fluid jet stream. More specifically, FIG. 4(a) is an example of the pulse laser beam intensity and the initial velocity of the fluid jet stream, and FIG. 4(b) is an example of the time-based change of the laser beam intensity and the liquid jet stream. In FIG. 4(a), the ordinate indicates the intensity I (w) of the laser beam, and the abscissa indicates the time T (s). In FIG. 4(b), the ordinate indicates the liquid jet stream velocity (liquid jet stream initial velocity) V0 (m/s).

In this embodiment, the control device 4 (controller) controls the laser device 2 so that the pulse laser beam having pulse width Tl (s) and repeat cycle TR (s) is irradiated from the laser beam irradiation part via the optical fiber, as shown in FIG. 4(a). The jet stream ejected from the nozzle has the liquid jet stream pulse width Tj.

Figure 3A:
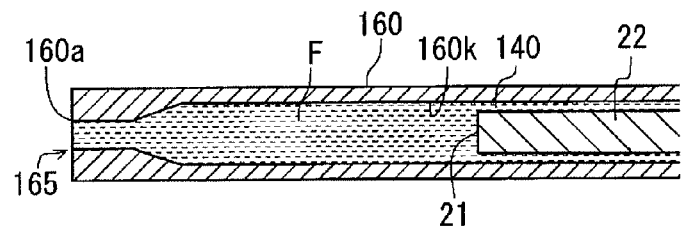
FIG. 3(a) is a diagram depicting an example of the operation of the jet stream generating device in a state before the pulse laser beam irradiation according to one or more embodiments of the present invention.
Figure 4A:
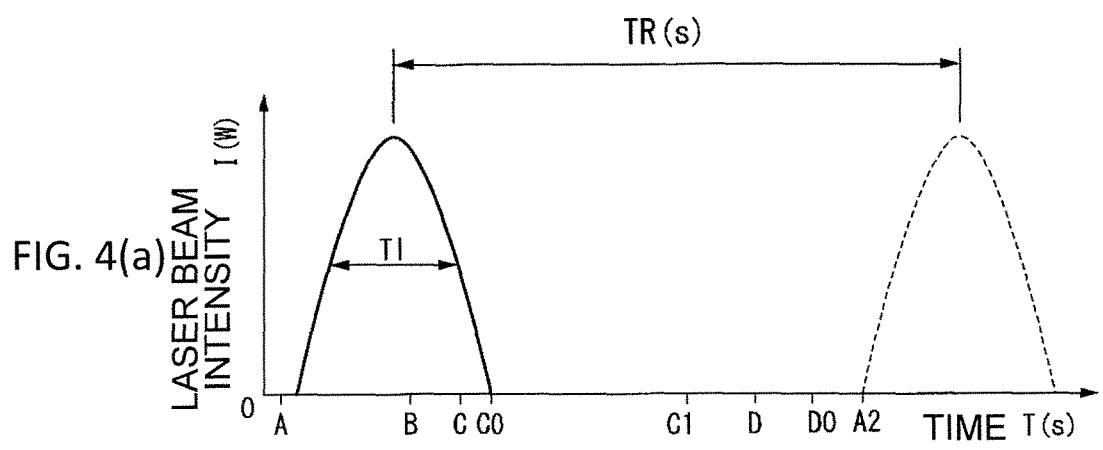
FIG. 4(a) is a diagram depicting an example of the pulse laser beam generated by the jet stream generating device and the initial velocity of the fluid jet stream according to one or more embodiments of the present invention.
Figure 4B:
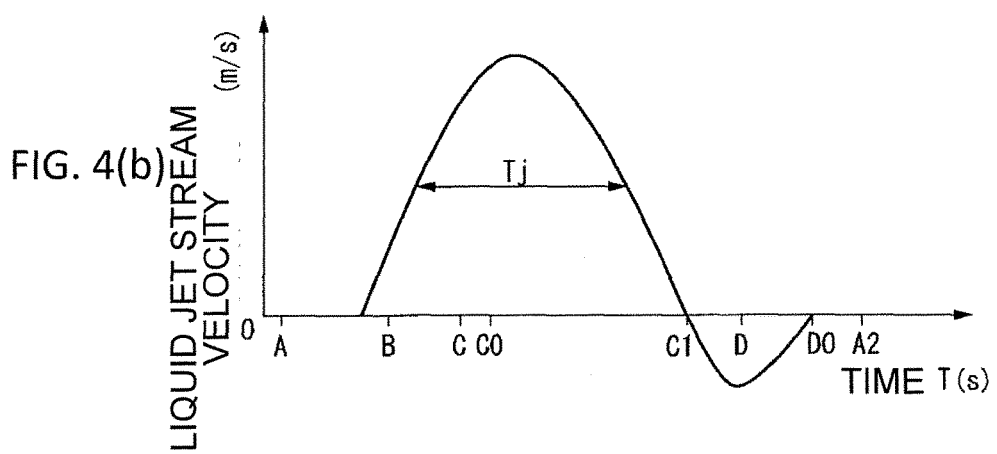
FIG. 4(b) is a diagram depicting an example of a time-based change of the intensity of the laser beam and the liquid jet stream according to one or more embodiments of the invention.

As shown in FIG. 3(a), if the laser beam is not irradiated from the laser beam irradiation part 21 at the tip part of the optical fiber 22 at time A shown in FIG. 4, the liquid F is filled into the cylindrical liquid chamber 160. Specifically, the liquid F is supplied from the supply part (liquid feeding device) into the cylindrical liquid chamber 160 via the liquid supply path 140, and fills the liquid chamber 160 up. In this case, the liquid F is not injected from the nozzle 165. In other words, the liquid jet stream velocity V0 is 0 (m/s). Concerning the timing when the supply part (liquid feeding device) supplies the liquid F into the cylindrical liquid chamber 160, a small amount (e.g. 0.2 cc/s) of the liquid F may be constantly supplied, for example, or the liquid F may be supplied only when the laser beam is not irradiated and the supply of the liquid F may be stopped when the laser beam is irradiated. In one or more embodiments of the invention, the control device 4 (controller) controls the supply timing of the liquid F appropriately depending on the intended use of the jet stream generating device 100.

Then the control device (controller) causes the laser device to irradiate a pulse laser beam. The pulse laser beam emitted from the laser device is guided into the liquid chamber 160 by the optical fiber 22, and is irradiated from the laser beam irradiation part 21 at the tip part of the optical fiber 22.

Figure 3B:
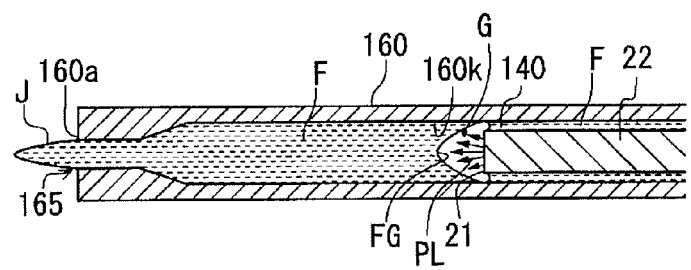
FIG. 3(b) is a diagram depicting an example of the operation of the jet stream generating device in an initial state of the pulse laser beam irradiation (initial state of bubble generation) according to one or more embodiments of the invention.

As shown in FIG. 3(b), if the pulse laser beam PL is irradiated from the laser beam irradiation part 21, the liquid F near the laser beam irradiation part 21 is heated by the laser beam and vaporized, and the bubble G is generated near the laser beam irradiation part 21. This liquid F has absorbency with respect to the laser beam. As this bubble G is generated, the pressure inside the cylindrical liquid chamber 160 increases, and the jet stream J of the liquid F is injected from the nozzle 165, which is disposed in the end part 160a of the cylindrical liquid chamber 160 (at time B shown in FIG. 4).

If the pulse laser beam PL is continuously irradiated from the laser beam irradiation part 21, the bubble G expands and the volume of the bubble G increases. As the bubble G, generated by the laser beam from the laser beam irradiation part 21, vaporizes and expands, the distance between the tip part of the optical fiber 22 to the boundary surface FG (gas-liquid interface) between the liquid F and the bubble G increases.

Figure 3C:
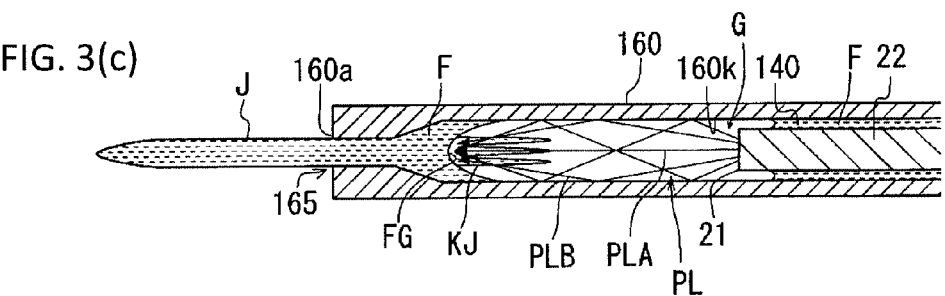
FIG. 3(c) is a diagram depicting an example of the operation of the jet stream generating device in a state when the pulse laser beam is irradiated and the bubble is expanded according to one or more embodiments of the invention.
Figure 3D:
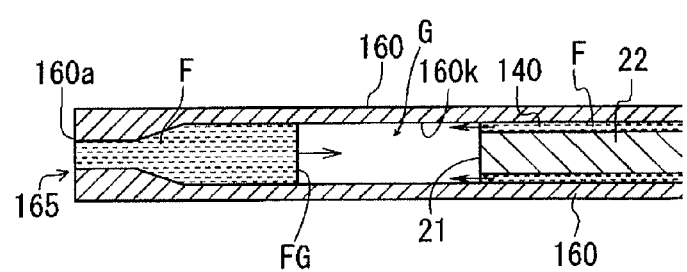
FIG. 3(d) is a diagram depicting an example of the operation of the jet stream generating device in a state when the pulse laser beam is not irradiated according to one or more embodiments of the invention.

Specifically, as shown in FIG. 3(c), there are two types of lights that are irradiated onto the boundary surface FG: light (direct light PLA) that is directly irradiated from the laser beam irradiation part 21 to the boundary surface FG (gas-liquid interface) through inside of the bubble G; and a light (reflected light PLB) which is irradiated from the laser beam irradiation part 21, reflected by the mirror plane 160k of the inner surface of the cylindrical liquid chamber 160, guided toward the end part 160a side of the cylindrical liquid chamber 160, and is irradiated onto the boundary surface FG (gas-liquid interface).

In this embodiment, the intensity of the reflected light is relatively high. Therefore, even if the distance from the tip part of the optical fiber 22 to the boundary surface FG (gas-liquid interface) between the liquid F and the bubble G increases due to the vaporizing and expansion of the bubble G, the intensity of the reflected light that is irradiated onto the boundary surface FG (gas-liquid interface) is high. In other words, even if the distance is large, the direct light and the reflected light having a relatively high intensity are irradiated onto the boundary surface FG (vaporization interface). Therefore, even if the distance is large, the vaporization effect on the boundary surface FG (gas-liquid interface) is high. In other words, the vaporization effect can be generated while the pulse laser beam follows the boundary surface FG (gas-liquid interface) in a state of maintaining high intensity until the irradiation of the pulse laser beam ends.

In other words, even if the above mentioned distance is relatively large, the pulse laser beam (direct light and reflected light) having a relatively high intensity is irradiated onto the boundary surface FG (gas-liquid interface) of the bubble G The pulse laser beam (the direct light and the reflected light) having relatively high intensity is irradiated onto the boundary surface FG (gas-liquid interface) of the bubble G, and this light energy is absorbed, whereby the vaporized jet KJ is injected in the opposite direction with respect to the opening side (nozzle side) of the cylindrical liquid chamber 160. Hence, the counteracting force generated by the vaporized jet is applied to the liquid F.

Even if the distance is large, the force generated by the expansion pressure of the bubble G and the force generated by the vaporized jet KJ both act on the liquid F. In other words, the injection of the liquid F is accelerated by the synergetic effect of the expansion pressure and the reactive force of the vaporizing jet KJ. In other words, even if the distance is large, the velocity of the jet stream from the nozzle 165 is high (e.g. as shown in time C in FIG. 4, for example).

Now if the intensity of the light irradiated from the laser beam irradiation part 21 at time C0 shown in FIG. 4 is zero, the expansion of the bubble G stops. After the expansion of the bubble G stops, the bubble G shrinking period starts (see FIG. 3(d)). The liquid jet stream velocity V0 decreases from the maximum value during the bubble G shrinking period.

Then at time C1 shown in FIG. 4, the liquid jet stream velocity V0 becomes zero. Then at time D shown in FIG. 4, the liquid jet stream velocity V0 becomes a minus value. In this case, the liquid F flows backward from the nozzle 165. To prevent the liquid jet stream velocity V0 from becoming a minus value, the control device 4 (controller) may perform control so that the liquid feeding device 1 supplies the liquid F into the liquid chamber 160 via the liquid supply path 140.

At time D0 shown in FIG. 4, the liquid jet stream velocity V0 (m/s) becomes zero. In this case, the bubble G disappears from the cylindrical liquid chamber 160, and the liquid chamber 160 is filled with the liquid F. Then at time A2, irradiation of the pulse laser beam is started again.

By forming the inner surface of the liquid chamber 160 to be the mirror plane 160k like this, less of the laser beam is absorbed by the inner surface of the liquid chamber 160, and the laser beam can be efficiently irradiated onto the gas-liquid interface.

Further, by forming the inner surface of the liquid chamber 160 to be the mirror plane 160k, an arbitrary laser beam can continuously and constantly reach the gas-liquid interface, therefore a stable arbitrary vaporized jet KJ can be continuously injected.

Furthermore, by forming the inner surface of the liquid chamber 160 to be the mirror plane 160k, the pulse liquid jet stream having high intensity can be jet streamed for a long time, even if the distance L1, from the optical fiber emit end to the nozzle, is large.

Figure 5:
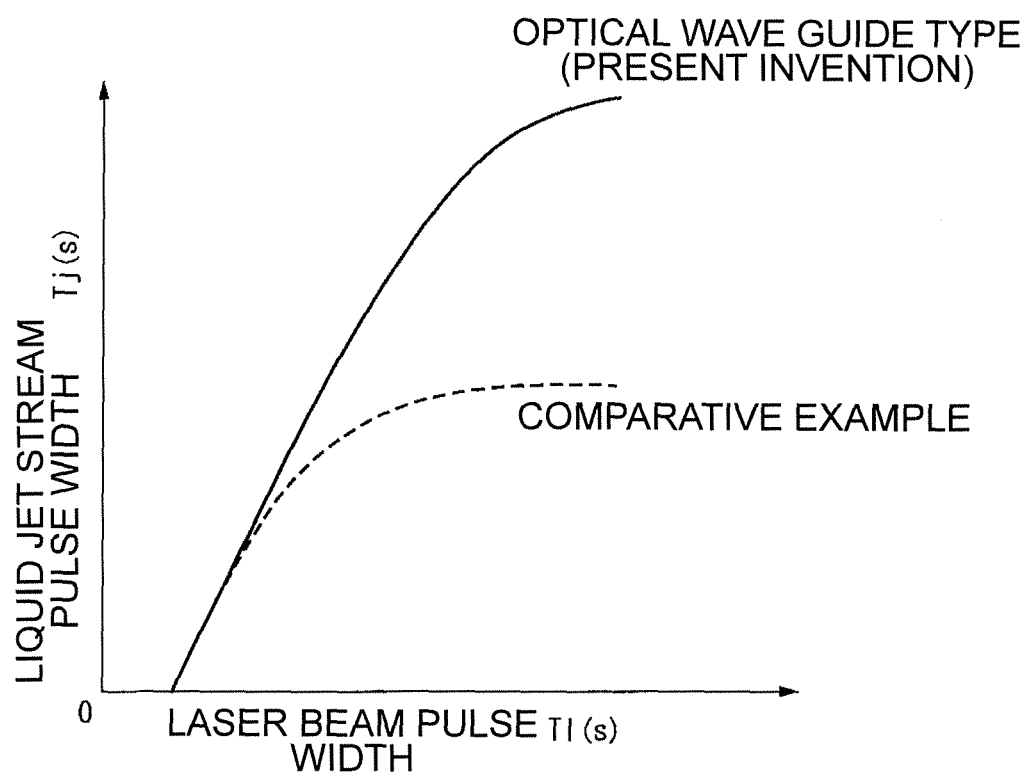
FIG. 5 is a conceptual diagram depicting an example of the dependency of the liquid jet stream pulse width on the laser beam pulse width in the jet stream generating device according to one or more embodiments of the present invention and the jet stream generating device according to a comparative example.
Figure 10A:
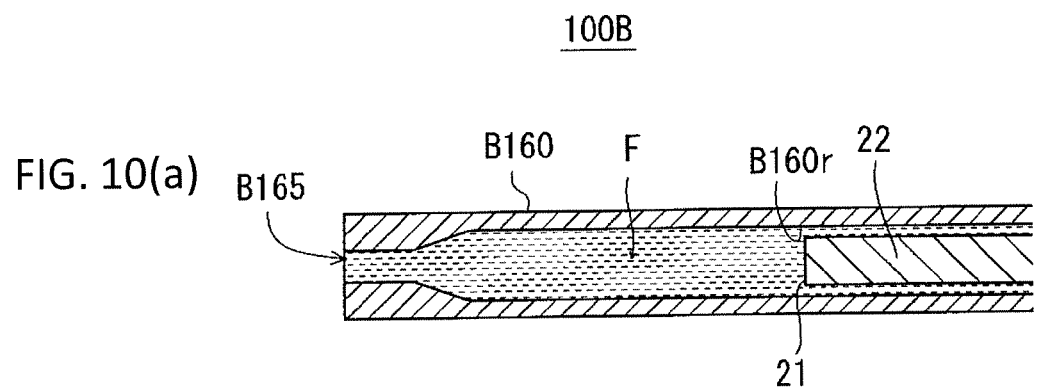
FIG. 10(a) is a diagram depicting an example of the operation of the jet stream generating device in a state before the pulse laser beam irradiation according to one or more embodiments of the invention.
Figure 10B:
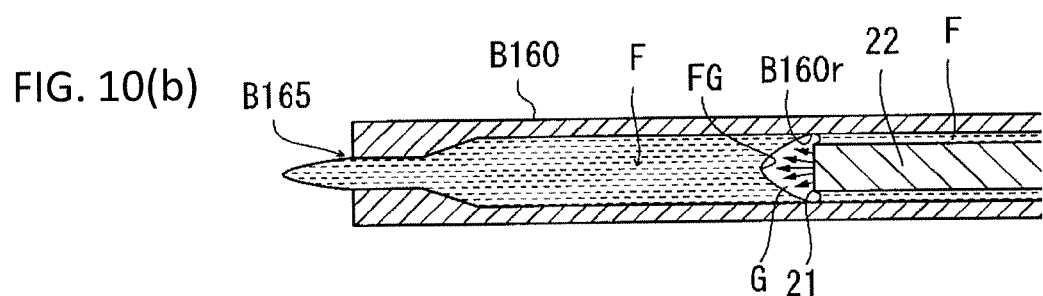
FIG. 10(b) is a diagram depicting an example of the operation of the jet stream generating device in an initial state of the pulse laser beam irradiation (initial state of bubble generation) according to one or more embodiments of the invention.
Figure 10C:
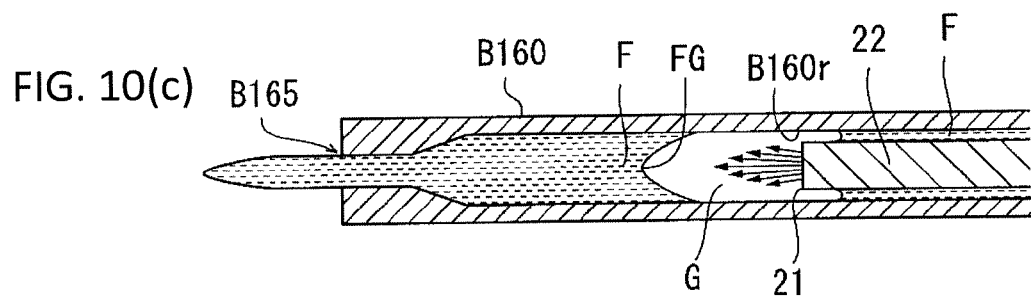
FIG. 10(c) is a diagram depicting an example of the operation of the jet stream generating device in a state when the pulse laser beam is irradiated and the bubble is expanded according to one or more embodiments of the invention.
Figure 11:
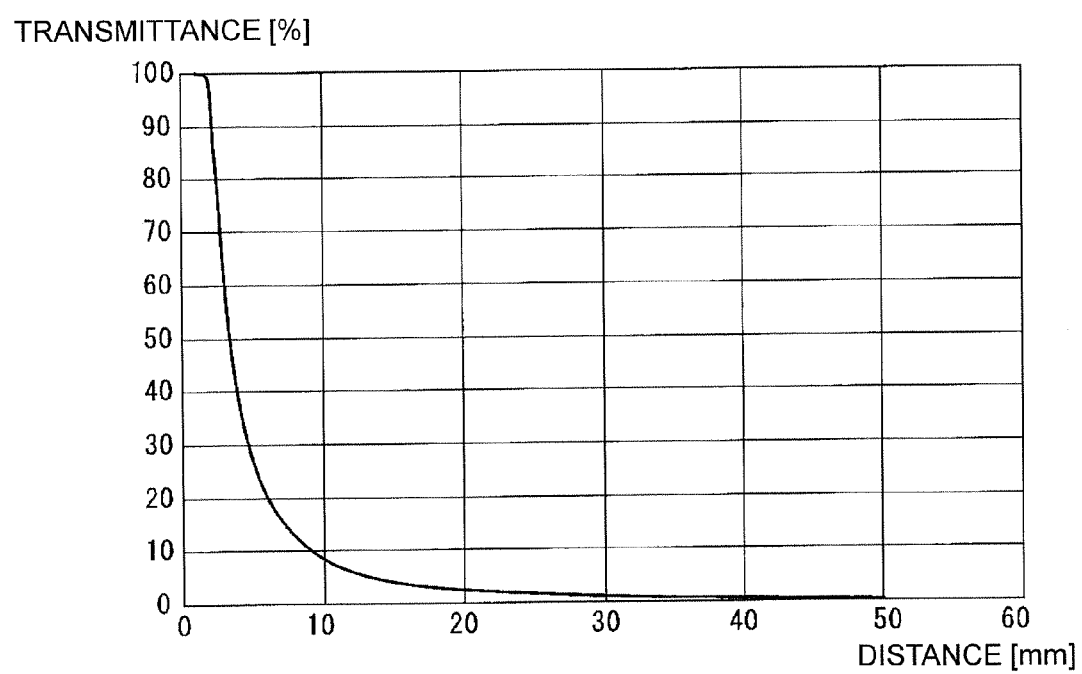
FIG. 11 is a diagram depicting an example of the relationship of the transmittance and the distance according to one or more embodiments of the invention.
Figure 12:
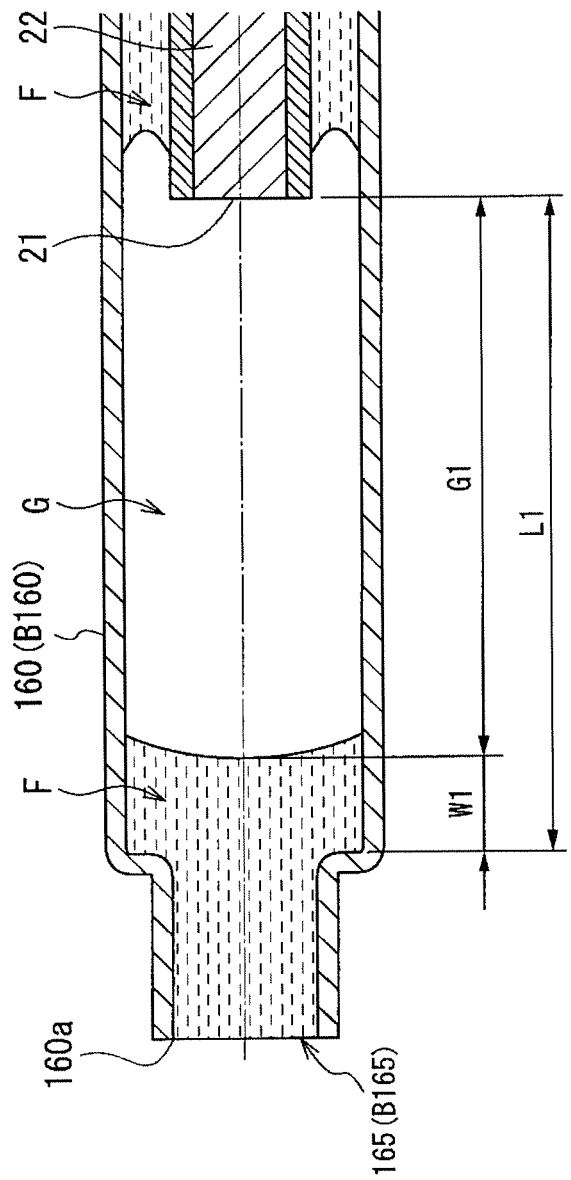
FIG. 12 is a diagram depicting an example of the jet stream generating device according to one or more embodiments of the invention.

FIG. 5 is a conceptual diagram depicting an example of the dependency of the laser beam pulse width on the liquid jet stream pulse width in the jet stream generating device 100 according to one or more embodiments of the present invention and the jet stream generating device 100B of a comparative example (see FIG. 10). In FIG. 5, the ordinate indicates the liquid jet stream pulse width Tj (s), and the abscissa indicates the laser beam pulse width Tl (s). In FIG. 5, the solid line indicates a curve related to the jet stream generating device 100 according to one or more embodiments of the present invention, and the dotted line indicates a curve related to the jet stream generating device 100B of the comparative example.

In the jet stream generating device 100B of the comparative example, a rough surface B160r is formed on the inner surface of the cylindrical liquid chamber B160 (see FIG. 10). In the case of the jet stream generating device 100B of the comparative example, the laser beam irradiated from the tip part of the optical fiber is more likely to be scattered and absorbed by the inner surface of the liquid chamber B160 because of the rough surface B160r. Therefore if the pulse width of the laser beam is increased, the liquid jet stream pulse width Tj (s) will never exceed a relatively small predetermined value. In other words, in the case of the jet stream generating device 100B of the comparative example, the upper limit value of the energy of the jet stream, that is injected from the nozzle, is relatively small.

In the jet stream generating device 100 according to one or more embodiments of the present invention, the mirror plane 160k is formed on the inner surface of the cylindrical liquid chamber 160 (see FIG. 2). Therefore in the case of the jet stream generating device 100, the value of the liquid jet stream pulse width Tj (s) becomes larger than that of the comparative example as the value of the pulse width Tl of the laser beam is greater, and the liquid jet stream pulse width Tj (s) becomes a large value without being saturated at the predetermined value of the comparative example. In other words, in the jet stream generating device 100 according to one or more embodiments of the present invention, the energy of the jet stream, that is injected from the nozzle 165, is relatively high.

Figure 6:
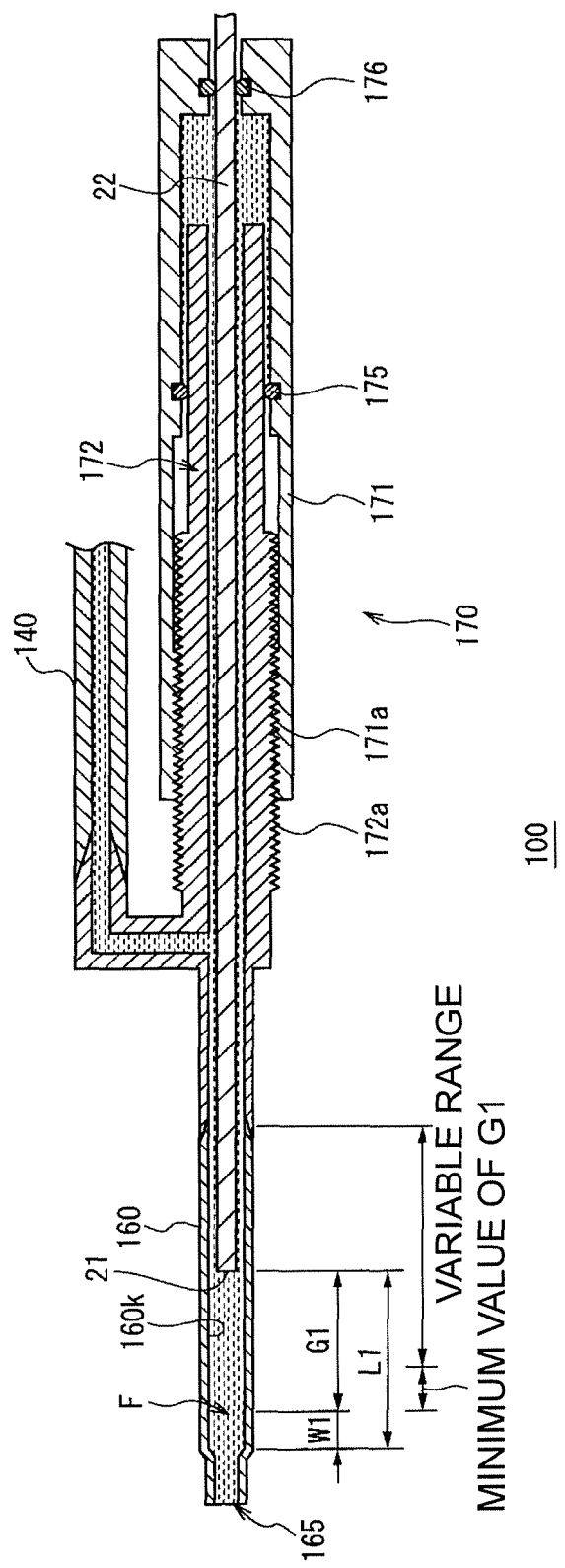
FIG. 6 is a diagram depicting a concrete example of the jet stream generating device according to one or more embodiments of the present invention.

FIG. 6 is a diagram depicting a concrete example of the jet stream generating device 100 according to one or more embodiments of the present invention. FIG. 7 shows an example of the operation of the adjusting part 170 of the jet stream generating device 100 shown in FIG. 6. Specifically, FIG. 7(a) is an example of a state when the tip part of the optical fiber 22 is moved toward the nozzle 165, and FIG. 7(b) is an example of a state when the tip part of the optical fiber 22 is moved toward the opposite side of the nozzle 165.

As mentioned above, the adjusting part 170 (adjuster) is configured to adjust the distance between the nozzle 165 and the laser beam irradiation part 21 disposed in the tip part of the optical fiber 22. A concrete example of the adjusting part 170 will be described.

In the examples shown in FIG. 6 and FIG. 7, the adjusting part 170 has a small diameter cylindrical part 172 and a large diameter cylindrical part 171 which functions as the optical fiber holding member. The small diameter cylindrical part 172 has a structure linked to the liquid chamber 160. The large diameter cylindrical part 171 is disposed on the outer periphery side of the small diameter cylindrical part 172. The small diameter cylindrical part 172 and the large diameter cylindrical part 171 are engaged by screw parts 172a and 171a, for example.

An opening part, to which the optical fiber 22 is inserted, is formed in the end part of the large diameter cylindrical part 171, and a sealing member 176, such as an O ring, is disposed in this opening part, so as to prevent the liquid F from flowing out. In this embodiment, a groove is formed in the opening part, and the sealing member 176 is disposed in the groove. This sealing member 176 contacts the optical fiber 22 in a roughly fixed state.

A sealing member 175, such as an O ring, is disposed between the small diameter cylindrical part 172 and the large diameter cylindrical part 171, so as to prevent the liquid F from flowing out. In this embodiment, a groove is formed on the inner peripheral surface of the large diameter cylindrical part 171, and the sealing member 175 is disposed in the groove. When the small diameter cylindrical part 172 and the large diameter cylindrical part 171 relatively move in the axis direction, the sealing member 175, such as an O ring, slides on the outer peripheral surface of the small diameter cylindrical part 172. A groove may be created in the end part of the small diameter cylindrical part 172, so that the sealing member 175, such as an O ring, is disposed in this groove.

As shown in FIG. 7(a) and FIG. 7(b), in this embodiment, when the small diameter cylindrical part 172 and the large diameter cylindrical part 171 relatively move in the axis direction, the laser beam irradiation part 21, disposed in the tip part of the optical fiber 22, can freely move within a variable range. The small diameter cylindrical part 172 and the large diameter cylindrical part 171 have a screw structure, and the position of the laser beam irradiation part 21 can be adjusted by rotating the large diameter cylindrical part 171 around the small diameter cylindrical part 172, with the axis direction as the rotation axis. For example, a driving motor may be used to rotate the large diameter cylindrical part 171 around the small diameter cylindrical part 172, with the axis direction as the rotation axis.

In this embodiment, the mirror plane 160k is formed on the inner surface of the liquid chamber 160 at least in the variable range of the tip part of the laser beam irradiation part 21 that emits the pulse laser beam.

In order to increase the pulse width of the jet stream outputted from the nozzle 165, the distance L1 from the laser beam irradiation part 21 disposed in the tip part of the optical fiber 22 to the nozzle 165 must meet condition A in terms of safety, that is, L1>G1, so that the expanded gas (bubble G) having high temperature and high pressure is not injected from the nozzle 165. G1 indicates the length of the expanded gas (bubble G of vapor), which is generated in the liquid chamber 160.

Further, the distance L1 from the optical fiber emit end to the nozzle must meet condition B, that is, W1=L1−G1 must be very small. W1 is a value determined by subtracting the length G1 of the expanded gas (bubble G) from the distance L1 between the optical fiber emit end and the nozzle when the expanded gas (bubble G) is generated, and corresponds to the length of the residual liquid in the tube near the nozzle. If W1 is large, the fluid resistance caused by the movement of water increases and the energy of the liquid jet is lost, hence it is advantageous that W1 is a small value, such as 5 mm to 15 mm. One example of the value is about 10 mm.

The jet stream generating device 100 according to one or more embodiments of the present invention can adjust L1, so that the pulse energy E0 and the pulse width T1 can be changed to satisfy condition A and condition B as the laser irradiation conditions.

Considering W1, in one or more embodiments of the invention, the variable range of the distance between the nozzle 165 and the laser beam irradiation part 21 is a range of the distance L1 between the nozzle 165 and the laser beam irradiation part 21, from which the minimum ranges of W1 and G1 are removed.

As described above, the jet stream generating device 100 (pulse jet knife) according to one or more embodiments of the present invention generates the intermittent jet stream utilizing the vaporizing expansion pressure, using the pulse laser beam emitted from the laser beam irradiation part 21, and changes the length of the liquid chamber 160 (expansion chamber) corresponding to the laser output (expansion chamber length variable type). Further, the jet stream generating device 100 has a reflection structure on the inner wall to transmit light in the long liquid chamber 160 (expansion chamber).

Specifically, in the jet stream generating device 100 according to one or more embodiments of the present invention, the mirror plane 160k is formed on the inner surface of the liquid chamber 160, and the adjusting part 170, to adjust the distance between the laser beam irradiation part 21 and the nozzle 165, is included. Therefore, even if it is set such that the laser beam having a large pulse width is emitted from the laser beam irradiation part 21, and the distance between the laser beam irradiation part 21 and the nozzle 165 is long, the light absorption by the inner surface of the liquid chamber 160 is very small, and the pulse laser beam is reflected by the mirror plane 160k of the liquid chamber 160 and guided toward the nozzle 165, which is disposed in the end part 160a of the cylindrical liquid chamber 160, whereby the bubble G can be expanded large, and the duration of the liquid jet stream can be made relatively long.

In other words, in the jet stream generating device 100 according to one or more embodiments of the present invention, the inner surface of the liquid chamber 160 is formed as the mirror plane 160k, and the adjusting part 170 can change the distance between the laser beam irradiation part 21 and the nozzle 165 in accordance with the pulse width of the pulse laser beam emitted from the laser beam irradiation part 21, whereby the duration of the liquid jet stream emitted from the nozzle can be controlled.

The jet stream generating device 100 according to one or more embodiments of the present invention controls the intensity of the pulse laser beam and the pulse width of the laser beam independently, whereby the liquid jet stream velocity which is in proportion to or approximately in proportion to the intensity of the pulse laser beam and the liquid jet stream duration which is in proportion to or approximately in proportion to the pulse width of the laser beam, can be variably controlled independently. A concrete example will be described next.

FIG. 8 is a set of diagrams depicting examples of time-based changes of the laser beam intensity and the liquid jet stream velocity. In FIG. 8, the abscissa indicates the time T (s). In FIG. 8(a), FIG. 8(c), FIG. 8(e) and FIG. 8(g), the ordinate indicates the intensity I (W) of the pulse laser beam. In FIG. 8(b), FIG. 8(d), FIG. 8(f) and FIG. 8(h), the ordinate indicates the velocity (initial velocity) V0 (m/s) of the liquid jet stream.

By setting the pulse width of the pulse laser beam relatively short, setting the laser beam intensity relatively low, and setting the distance between the laser beam irradiation part 21 and the nozzle 165 relatively short using the adjusting part 170, a jet stream, of which jet stream velocity is relatively low and duration is short, can be generated (see FIG. 8(a), FIG. 8(b)).

By setting the pulse width of the pulse laser beam relatively long, setting the laser beam intensity relatively low, and setting the distance between the laser beam irradiation part 21 and the nozzle 165 relatively long, a jet stream, of which jet stream velocity is relatively low and duration is long, can be generated (see FIG. 8(c), FIG. 8(d)).

By setting the pulse width of the pulse laser beam relatively short, setting the laser beam intensity relatively high, and setting the distance between the laser beam irradiation part 21 and the nozzle 165 relatively short, a jet stream, of which jet stream velocity is relatively high and duration is short, can be generated (see FIG. 8(e), FIG. 8(f)).

By setting the pulse width of the pulse laser beam relatively long, setting the laser beam intensity relatively high, and setting the distance between the laser beam irradiation part 21 and the nozzle 165 relatively long, a jet stream, of which jet stream velocity is relatively high and duration is long, can be generated (see FIG. 8(g), FIG. 8(h)).

As mentioned above, the jet stream generating device 100 can variably control the velocity (initial velocity) of the liquid jet stream emitted from the nozzle and the duration of the liquid jet stream independently. This is very effective when the jet stream generating device 100 is applied to a pulse jet knife which crushes biotissue, for example.

Specifically, the surgical instrument (pulse jet knife) using pulse liquid jet stream determines the crushing or preserving of biotissue utilizing the difference of elasticity characteristics of biotissue.

The crushing force (impulsive force) of the liquid jet stream is referred to as an "impulse", which is a product of the large force generated when the liquid jet stream acts on the biotissue, and the short duration when the liquid jet stream acts on the biotissue (jet stream time).

In concrete terms, when the sectional area of the nozzle (sectional area of the liquid jet stream) is constant, the velocity (initial velocity) of the liquid jet stream is in proportion to the force of the liquid jet stream. Therefore the product of the velocity (initial velocity) of the liquid jet stream and the duration of the liquid jet stream is in proportion to the impulse. Therefore the crushing force (impulsive force) of the liquid jet stream is in proportion to the product of the velocity (initial velocity) of the liquid jet stream and the duration thereof.

To determine the boundary conditions of the biotissue between crushing and preserving using the pulse jet knife, by finely controlling the crushing force of the liquid jet stream to the biotissue, it is very important to variably control the velocity (initial velocity) of the liquid jet stream and the duration of the liquid jet stream. As mentioned above, the jet stream generating device 100 according to one or more embodiments of the present invention has the mirror plane 160k formed on the inner surface of the liquid chamber 160, and includes the adjusting part 170 to adjust the distance between the laser beam irradiation part 21 and the nozzle 165, and can independently control the velocity (initial velocity) of the liquid jet stream and the duration thereof by adjusting the above mentioned distance and adjusting the intensity and the pulse width of the pulse laser beam, therefore the jet stream generating device 100 is useful for a pulse jet knife or the like.

An example of the method of using the jet stream generating device 100 as the pulse jet knife will be described.

In the case of surgery to crush a thrombosis or the like, a pulse laser beam having low intensity is outputted from the laser beam irradiation part 21 for a short time, and a jet stream having low jet stream pressure is applied to the segment for a predetermined time, whereby surgery can be performed with minimal damage to a portion to be preserved.

If the intensity of the pulse laser beam is gradually increased to gradually increase the intensity of the jet stream during a surgery, the damage to the portion to be preserved can be minimized, and thrombosis or the like can be removed with certainty. If the intensity and the pulse width of the pulse laser beam are adjusted using the pulse laser beam irradiation part, and the duration of the jet stream is controlled by adjusting the distance between the nozzle and the laser beam irradiation part using the adjusting part 170, so as to generate a jet stream which can cut at high intensity for a short time, then such a segment as a thrombosis can be efficiently crushed. Further, if the intensity and the pulse width of the pulse laser beam is adjusted by the pulse laser beam irradiation part and the duration of the jet stream is adjusted by the adjusting part 170 during surgery after the crushing of the thrombosis is confirmed, then damage to the preserving segment can be easily minimized.

As described above, in the case of the pulse jet knife using the jet stream generating device 100 according to one or more embodiments of the present invention, the crushing force can be finely controlled by: the pulse laser beam irradiation part which controls the intensity of the jet stream by adjusting the intensity and pulse width of the pulse laser beam; and the adjusting part 170 which variably controls the duration of the jet stream, whereby the crushing segment and the preserving segment of the biotissues can be easily distinguished even if the difference between the elastic characteristics of the crushing segment and that of the preserving segment are very little. Further, the intensity and duration of the jet stream can be freely and independently controlled during surgery, hence various surgical techniques can be implemented.

The adjusting part 170 is not limited to the above mentioned configuration, but it is sufficient if a mechanism to adjust the distance between the nozzle 165 and the laser beam irradiation part 21 is included.

FIG. 9 is a set of diagrams depicting an example of the jet stream generating device 100 having a rotation stopping member 179. Specifically, FIG. 9(a) is a lateral cross-sectional view of the jet stream generating device 100, and FIG. 9(b) is a cross-sectional view along the A-A line of FIG. 9(a).

In the examples shown in FIG. 9, the adjusting part 170 has a small diameter cylindrical part 172 which is linked to the liquid chamber 160, a cylindrical part 178 which holds the optical fiber 22, a rotation member 177, and a rotation stopping member 179 among others.

The small diameter cylindrical part 172 is linked to the liquid chamber 160. The cylindrical part 178 is disposed along the axis direction of the small diameter cylindrical part 172 with a predetermined distance from the small diameter cylindrical part 172.

A cylindrical rotation member 177 is disposed on the outer periphery side of the small diameter cylindrical part 172 and the cylindrical part 178. The rotation member 177 and the small diameter cylindrical part 172 are configured to engage with each other by screw parts 177a and 172a, and the rotation member 177 and the cylindrical part 178 are configured to engage with each other by screw parts 177b and 178b. The screw parts 177a and 172a and the screw parts 177b and 178b are configured to be counter-screws of each other respectively.

An opening part, to which the optical fiber 22 is inserted, is formed in the end part of the cylindrical part 178, and a sealing member 176, such as an O ring, is disposed in the opening part, whereby the sealing member 176 is contacted with the optical fiber 22 in a roughly fixed state.

One or a plurality of sealing member(s) 175, such as an O ring, is/are disposed between the rotation member 177 and the small diameter cylindrical part 172, and one or a plurality of sealing members 174, such as an O ring, is/are disposed between the rotation member 177 and the cylindrical part 178, so as to prevent the liquid F from flowing out.

The adjusting part 170 shown in FIG. 9 is configured such that when the rotation member 177 rotates normally or rotates in reverse around the axis as the rotation center, and the small diameter cylindrical part 172 and the cylindrical part 178 move in approaching directions or in departing directions. Further, in this embodiment, even if the small diameter cylindrical part 172 and the cylindrical part 178 move in approaching directions or in departing directions along the axis direction, the rotation stopping member 179 prevents the small diameter cylindrical part 172 and the cylindrical part 178 from relatively rotating around the axis as the rotation center.

The rotation stopping member 179 is formed to have a U-shaped cross-section, for example, where the end part 179b on the nozzle side and the end part 179c on the other side are linked by a linking part 179a. The end part 179b on the nozzle side is fixed to the small diameter cylindrical part 172. The cylindrical part 178 is inserted, with an interval, in the opening part 179h formed on the other end part 179c, so that the cylindrical part 178 is held by the end part 179c to be freely movable in the axis direction.

A groove 178u is formed on the outer periphery of the cylindrical part 178, and the groove 178u extends in the axis direction. A protrusion 179t, which is formed on the inner periphery of the opening part 179h of the end part 179c of the rotation stopping member 179, is engaged with the groove 178u, so as to prevent the rotation of the cylindrical part 178 around the axis as the rotation center. The protrusion 179t can easily be formed by disposing such a member as a set screw 179n, for example.

A scale may be disposed in visible portions of the outer periphery of the rotation member 177 and the outer periphery of the small diameter cylindrical part 172 (or the cylindrical part 178), so as to recognize the rotation angle of the rotation member 177 with respect to the small diameter cylindrical part 172 (or the cylindrical part 178).

The rotation angle of the rotation member 177, with respect to the small diameter cylindrical part 172, corresponds to the moving distances of the small diameter cylindrical part 172 and the cylindrical part 178 in the approaching directions or in the departing directions, in other words, the moving distance of the laser beam irradiation part 21 disposed in the tip part of the optical fiber 22.

By disposing this scale, the moving distance of the laser beam irradiation part 21, disposed in the tip part of the optical fiber 22, can easily be quantitatively recognized based on the rotation angle of the rotation member 177.

In the above embodiment, the groove 178*u* of the cylindrical part 178 and the protrusion 179*t* of the rotation stopping member 179 engage with each other, but the present invention is not limited to this, since a groove may be disposed on the inner periphery of the opening part 179*h* of the rotation stopping member 179, and a protrusion may be disposed on the outer periphery of the cylindrical part 178 so as to prevent the rotation of the cylindrical part 178.

As described above, the jet stream generating device 100 according to an embodiment of the present invention generates a jet stream of the liquid F. This jet stream generating device 100 has: the cylindrical liquid chamber 160 such as a metal cylindrical member; the nozzle 165 which is an opening part disposed in the end part of the liquid chamber 160, and injects the liquid F in the liquid chamber 160 to outside; the liquid supply patch 140 configured to supply the liquid F into the liquid chamber 160; and the laser beam irradiation part 21 configured to irradiate a pulse laser beam into the liquid chamber 160, and generates the bubble G by vaporizing the liquid F inside the liquid chamber 160. The inner surface of the liquid chamber 160 has the mirror plane 160*k* which reflects the pulse laser beam emitted from the laser beam irradiation part 21, and guides the pulse laser beam to the end part 160*a* of the liquid chamber 160. In other words, the cylindrical liquid chamber 160, such as a metal cylindrical member, functions as the optical wave guide (light guide tube). Further, the jet stream generating device 100 has the laser device 2 (laser oscillator) configured to control the laser beam intensity and the laser beam pulse width independently.

When the pulse laser beam is irradiated, the pulse laser beam heats the irradiated liquid F, and vaporizes the liquid F, whereby the bubble G is generated. In this embodiment, the light is reflected by the mirror plane of the liquid chamber 160, and the intensity of the light is relatively high. Therefore even if the distance from the tip part of the optical fiber 22 to the boundary surface FG (gas-liquid interface) of the liquid F and the bubble G increases due to the vaporizing expansion of the bubble G, the intensity of the reflected light irradiated onto the boundary surface FG (gas-liquid interface) is high. In other words, even if this distance is large, the direct light and reflected light having relatively high intensity are irradiated onto the boundary surface FG (vaporization interface).

Therefore even if this distance is large, the vaporization action on the boundary surface FG (gas-liquid interface) is strong. In other words, until the irradiation of the pulse laser beam ends, the pulse laser beam causes the vaporization action while following along the boundary surface FG (gas-liquid interface) in a state of maintaining high intensity. The pulse laser beam having relatively high intensity (direct light and reflected light) is irradiated onto the boundary surface FG (gas-liquid interface) of the bubble G. Therefore even if this distance is large, the force caused by the expansion pressure of the bubble G and the force caused by the vaporizing jet act on the liquid F. In other words, the jet stream velocity of the liquid from the nozzle 165 is high, even if this distance is large, because of the synergetic effect of the expansion pressure and the reactive force of the vaporized jet.

The jet stream generating device 100 according to an embodiment of the present invention also includes the adjusting part 170 (adjuster) configured to adjust the distance between the nozzle 165 and the laser beam irradiation part 21. Specifically, the adjusting part is configured to freely adjust the laser beam irradiation part 21 disposed in the tip part of the optical fiber 22 in the movable range inside the liquid chamber 160. In concrete terms, the adjuster is configured to freely adjust the distance between the nozzle 165 and the laser beam irradiation part 21 in accordance with the pulse width of the pulse laser beam (or the energy of the pulse laser beam) emitted from the laser beam irradiation part 21. The mirror plane 160*k* is formed on the inner surface of the liquid chamber 160 at least in the variable range in the tip part of the laser beam irradiation part 21 to emit the pulse laser beam.

By forming the mirror plane 160*k* on the inner surface of the liquid chamber 160, the laser beam can be continuously and constantly irradiated onto the gas-liquid interface, hence the vaporized jet KJ can be stably emitted for a long time. Furthermore, the distance L1 from the laser beam irradiation part 21, disposed in the tip part of the optical fiber 22, to the nozzle 165 can be freely set using the adjusting part 170 (adjuster), therefore the provided surgical device (pulse jet knife) can use a pulse liquid jet stream having an optimum jet stream intensity for the elastic differences generated by the individual difference or segmental difference (e.g. organ, position of organ) of the biotissues or the elastic differences generated by the pathological progression state of the affected segment.

Further, as mentioned above, the distance L1 from the laser beam irradiation part 21, disposed in the tip part of the optical fiber, to the nozzle 165 must meet condition A in terms of the safety required for the jet stream generating device 100, that is, L1>G1, so that the expanded gas (bubble G) having a high temperature and high pressure is not injected from the nozzle, and the distance L1 from the laser beam irradiation part 21, disposed in the tip part of the optical fiber 22 to the nozzle 165, must meet condition B, that is, W1=L1−G1. If W1 is large, the fluid resistance caused by the movement of the water increases, and the energy of the liquid jet is lost, hence W1 may be a small value, such as 5 mm to 15 mm. An example of the value is about 10 mm.

According to an embodiment of the present invention, the adjusting part 170 (adjuster) adjusts the distance L1 while satisfying condition A and condition B, whereby the pulse energy E0 and pulse width T1 can be set to desirable values as the laser irradiation conditions.

For example, in the case of the jet stream generating device of a comparative example, where the position of the tip part of the optical fiber 22 is fixed, the distance L1 cannot be adjusted as mentioned above, and E0 and T1 cannot be set to the desirable values as the laser irradiation conditions.

In the case of the jet stream generating device of a comparative example, where a reinforcing member constituted by a material having a high melting point, to withstand the heat generated by the optical fiber, and a predetermined rigidity, is disposed on the inner surface of the tube near the laser beam irradiating position, the optical wave guide structure is not created and the distance L1 cannot be adjusted, therefore E0 and T1 cannot be set to the desired values as the laser irradiation conditions.

In the case of the jet stream generating device of a comparative example, where the jet generating tube part, in which the optical fiber is inserted, is included, and the jet generating tube part is constituted by such materials as gold or platinum, so as to withstand the heat generated by the laser beam and heat induced by the laser beam which is irradiated internally, the distance L1 cannot be adjusted, and E0 and T1 cannot be set to the desired values as the laser irradiation conditions.

In the case of the jet stream generating device 100 according to an embodiment of the present invention, the mirror plane 160k on the inner surface of the cylindrical liquid chamber 160 is a surface treated by an electrolytic polishing treatment, reaming treatment, plating treatment, vapor deposition treatment, abrasive blowing treatment or the like. Specifically, the mirror plane 160k can easily be formed on the inner surface of the liquid chamber 160 by performing the various above mentioned treatments for the cylindrical liquid chamber 160 having a rough inner surface, for example.

In the jet stream generating device 100 according to an embodiment of the present invention, the pulse laser beam irradiated by the laser beam irradiation part is reflected by the mirror plane 160k of the liquid chamber 160 at a predetermined value or higher reflectance. This predetermined value or higher reflectance is a reflectance that allows the mirror plane 160k to reflect the pulse laser beam emitted from the laser beam irradiation part 21, and guide it to the end part 160a of the cylindrical liquid chamber 160. Since the jet stream generating device 100 includes the cylindrical liquid chamber 160 having the mirror plane 160k, of which reflectance is the predetermined value or higher, the pulse laser beam emitted from the laser beam irradiation part 21 can easily be reflected and guided to the end part 160a of the cylindrical liquid chamber 160.

In the jet stream generating device 100 according to an embodiment of the present invention, the cylindrical liquid chamber 160 may be a circular cylindrical member, as mentioned above. The cylindrical liquid chamber 160 having a circular cylindrical shape has high propagation efficiency with respect to the pulse laser beam, compared with a polygonal cylindrical shape, such as a triangular cylindrical shape or square cylindrical shape. Therefore even if the bubble G in the circular cylindrical liquid chamber 160 expands and the distance from the tip part of the optical fiber 22 to the boundary surface FG between the liquid F and the bubble G, which is gas, becomes relatively large, the pulse laser beam having high intensity can be irradiated onto the boundary surface FG (gas-liquid interface).

As mentioned above, a material constituting the cylindrical liquid chamber 160 of the jet stream generating device 100 according to an embodiment of the present invention can be such metals as stainless steel, titanium, gold, platinum, silver, copper and aluminum, or ceramics. For the material constituting the cylindrical liquid chamber 160, one of these materials may be used, or two or more thereof may be combined. If the cylindrical liquid chamber 160 is constituted by these materials, a jet stream generating device 100, which can withstand the pressure in the cylindrical liquid chamber 160 even when the bubble G is generated, when the bubble is expanded, and when the liquid jet stream is injected, can be provided. Further, by using the above mentioned materials for the cylindrical liquid chamber 160, the mirror plane 160k can easily be formed on the inner surface of the liquid chamber 160.

The jet stream generating device 100 according to an embodiment of the present invention has the liquid feeding device 1, which is a supply part configured to supply the liquid F into the liquid chamber 160 via the liquid supply path 140, synchronizing with the irradiation of the pulse laser beam by the laser beam irradiation part 21. This liquid feeding device 1 replenishes the liquid F immediately before the laser beam irradiation, so that the liquid chamber 160 is filled with the liquid F. Specifically, if the intensity of the laser pulse beam becomes zero after the bubble G is generated by the irradiation of the laser pulse beam, the bubble G shrinks and disappears. The liquid feeding device 1 replenishes the liquid F when the laser beam is not irradiated. In this embodiment, the distance SD between the end part 160a of the liquid chamber 160 and the tip of the optical fiber 22 is relatively long, and a sufficient amount of water required for one pulse is secured, hence the jet stream pulse data Tj can be increased. Further, the liquid F, for the amount required for one pulse, is supplied from the liquid feeding device 1 only when the laser beam is not irradiated, hence the pulsed jet stream can be stably injected from the nozzle 165. If the liquid F back-flows from the nozzle 165 into the cylindrical liquid chamber 160, the liquid feeding device 1 may control the flow rate of the liquid F in accordance with the amount of the back flow. The supply part (liquid feeding device 1) may constantly supply a small amount (e.g. 0.2 cc/s=0.2 ml/s) of liquid F to the cylindrical liquid chamber 160. It is sufficient if the cylindrical liquid chamber 160 is filled with the liquid F immediately before the laser beam is irradiated.

In the jet stream generating device 100 according to an embodiment of the present invention, the optical fiber 22 is the means of guiding the pulse laser beam from the laser device 2 into the liquid chamber 160. By using the optical fiber 22, the pulse laser beam emitted from the laser device 2 can be guided into the liquid chamber 160 at high efficiency. If the jet stream generating device 100 is applied to a surgical instrument, the use of the optical fiber 22, which has flexibility, improves the operability of the Y connector 120.

As mentioned above, the jet stream generating device 100 according to an embodiment of the present invention has a control device 4 as a controller to change the pulse energy, pulse width and pulse repeat frequency of the pulse laser beam irradiated by the laser beam irradiation part 21, and to control one, a set of, or all of the amount of the jet stream, flow rate of the jet stream, and repeat frequency of the jet stream. By the control device 4 performing the control to change the pulse energy, pulse width and pulse repeat frequency of the pulse laser beam emitted from the laser device 2, a desired amount of the jet stream, a desired flow rate, and a desired repeat frequency of the jet stream can be set for the jet stream injected from the nozzle 165.

For the liquid F used for the jet stream generating device 100 according to an embodiment of the present invention, water, saline solution, electrolytes and the like can be used. In this case, if a laser oscillator (laser device 2) that generates the holmium YAG laser (2.1 μm wavelength) is used for the pulse laser beam, the pulse laser beam having this wavelength is more easily absorbed by the liquid F, such as water, saline solution, electrolytes or the like. If the jet stream generating device 100 is used as a surgical instrument, the above mentioned liquid F may be used. However, the liquid F used for the jet stream generating device 100 according to an embodiment of the present invention is not limited to water, saline solution, electrolytes or the like, but another desired liquid F can be used depending on the application of the jet stream generating device 100.

In the case of using the jet stream generating device 100 according to an embodiment of the present invention for a surgical instrument, a calculus or hard tissue of a living body may be cut and crushed using the jet stream from the nozzle 165. When surgery to cut and crush a relatively hard calculus and hard tissue is performed, the jet stream generating device 100 can inject the jet stream at a relatively high velocity, and can set an optimum amount of the jet stream, an optimum flow rate of the jet stream, and an optimum repeat frequency of the jet stream as required. Therefore by using the jet stream generating device 100, surgery to cut and crush a calculus and hard tissue of a living body can be performed at high efficiency.

Further, in the case of using the jet stream generating device 100 according to an embodiment of the present invention for a surgical instrument, a biotissue may be cut and crushed using the jet stream from the nozzle 165. When surgery to cut and crush a relatively soft biotissue is performed, the jet stream generating device 100 can set an optimum amount of the jet stream, an optimum flow rate of the jet stream, and an optimum repeat frequency of the jet stream as required. Therefore by using the jet stream generating device 100, surgery to cut and crush biotissue can be performed at high efficiency.

Further, in the case of using the jet stream generating device 100 according to an embodiment of the present invention for a surgical instrument, a thrombosis blocking a blood vessel may be crushed using the jet stream from the nozzle 165. In this case, if a cylindrical liquid chamber 160 (thin metal tube) having a diameter smaller than the blood vessel is used, the thin metal tube can be inserted into the blood vessel, and surgery to crush the thrombosis or the like blocking the blood vessel can easily be performed, setting an optimum amount of the jet stream, an optimum flow rate of the jet stream, and an optimum repeat frequency of the jet stream for the surgery.

According to an embodiment of the present invention, if the jet stream generating device is used for a surgical instrument, the jet stream can be intermittently generated, therefore the propagation range of the pressure wave in the living body can be limited, and damage to a distant segment by pressure can be prevented, whereby safety increases.

Further, according to an embodiment of the present invention, if the liquid jet stream is used for a surgical instrument, the crushing region and preserving region can be finely controlled by finely controlling the differentiation of the cutting and crushing effect by the liquid jet stream utilizing the elastic differences of biotissues, and cutting, crushing or preserving complicated forms of biotissues can be performed without depending on the skill of a surgeon.

In the jet stream generating method of the jet stream generating device configured to generate a jet stream of liquid, the jet stream generating device 100 includes the adjusting part 170 (adjuster) and the like, and the adjusting part 170 (adjuster) adjusts the distance between the nozzle 165 and the laser beam irradiation part 21 before or at the irradiation of the pulse laser beam by the laser beam irradiation part 21. Therefore by the adjusting part 170 adjusting this distance before or at the irradiation of the pulse laser beam, a jet stream having a desired jet stream velocity, a desired pulse width and a desired jet stream energy can easily be generated while satisfying condition A and condition B.

Embodiments of the present invention were described with reference to the drawings. Any concrete configuration is not limited to the embodiments, but changes in the design within a scope that does not depart from the spirit of the invention are included in the present invention.

The content described in the embodiments with reference to each drawing can be combined unless an inconsistency or problem is generated in the objects and configurations thereof.

The content described with reference to each drawing could be an independent embodiment respectively, and the embodiment of the present invention is not limited to one embodiment that combines the content described with reference to each drawing.

The adjusting part 170 (adjuster) is not limited to the above mentioned structure. The rotation stopping member 179 is also not limited to the above mentioned structure. Any structure having the respective function is acceptable.

The adjusting unit 170 (adjuster) may be configured to manually adjust the distance between the nozzle 165 and the laser beam irradiation part 21.

The jet stream generating device 100 according to one or more embodiments of the invention has the nozzle 165 which has one hole opened at the end part 160a of the cylindrical liquid chamber 160 (metal tube), but the present invention is not limited to this embodiment. For example, the nozzle 165 may be disposed near the end part of the cylindrical liquid chamber 160, at the center of the cylindrical liquid chamber 160 in the axis direction, near the center of the cylindrical liquid chamber 160 in the axis direction or the like. The nozzle 165 may have a single hole or a plurality of holes.

In one or more embodiments of the invention, the jet stream generating device 100 is configured such that the liquid F flows in the nozzle direction by the bubble G generated in the cylindrical liquid chamber 160, and does not back-flow toward the fluid supply direction. Specifically, the jet stream generating device 100 is configured such that the flow resistance specified by the inner diameter Pz of the cylindrical liquid chamber 160, the diameter Az of the optical fiber, and the length AL of the optical fiber 22 (optical fiber insertion length) in the cylindrical liquid chamber 160 becomes sufficiently larger than the flow resistance specified by the injection nozzle parameters (diameter Nz of the nozzle 165 and length NL of the nozzle 165 having the diameter Nz in the axis direction). Thereby, a return (back-flow) of the liquid F toward the optical fiber side can be minimized.

Embodiments of the present invention were described above, and a part or all of the embodiments of the present invention are described in the Additions herein below.

[Addition 1]

A jet stream generating device configured to generate a jet stream of liquid, having:

a cylindrical liquid chamber;

a nozzle configured to open an end part of the liquid chamber and inject liquid in the liquid chamber to outside;

a liquid supply path configured to supply liquid into the liquid chamber;

a laser beam irradiation part configured to irradiate a pulse laser beam into the liquid chamber, and vaporize the liquid in the liquid chamber; and a laser oscillator configured to control laser beam intensity and laser beam pulse width independently, wherein an inner surface of the liquid chamber has a mirror plane for reflecting and guiding the pulse laser beam emitted from the laser beam irradiation part to the end part, and an adjuster configured to adjust a distance between the nozzle and the laser beam irradiation part is included.

[Addition 2]

The jet stream generating device according to Addition 1, wherein the adjuster adjusts the distance in accordance with the pulse width of the pulse laser beam emitted from the laser beam irradiation part.

[Addition 3]

The jet stream generating device according to Addition 1 or 2, wherein the mirror plane is a surface treated by at least one of: an electrolytic polishing treatment, a reaming treatment, a plating treatment, a vapor deposition treatment, and an abrasive blowing treatment.

[Addition 4]

The jet stream generating device according to any one of Additions 1 to 3, wherein the mirror plane is formed on the inner surface of the liquid chamber throughout at least a variable range in a tip part of the laser beam irradiation part that emits a pulse laser beam.

[Addition 5]

The jet stream generating device according to any one of Additions 1 to 4, wherein the liquid in the liquid chamber has energy absorbency with respect to a pulse laser beam irradiated from the laser beam irradiation part.

[Addition 6]

The jet stream generating device according to any one of Additions 1 to 5, wherein the mirror plane of the liquid chamber has a reflectance not less than a predetermined value with respect to a pulse laser beam irradiated from the laser beam irradiation part.

[Addition 7]

The jet stream generating device according to any one of Additions 1 to 6, wherein the liquid chamber is a circular cylindrical member.

[Addition 8]

The jet stream generating device according to any one of Additions 1 to 7, wherein a material constituting the cylindrical liquid chamber is such metals as stainless steel, titanium, gold and silver, or ceramics.

[Addition 9]

The jet stream generating device according to any one of Additions 1 to 8, further having a supply part (liquid feeding device) configured to supply liquid into the liquid chamber via the liquid supply path, synchronizing with the irradiation of a pulse laser beam by the laser beam irradiation part, and fill the liquid chamber with liquid immediately before the irradiation of the pulse laser beam.

[Addition 10]

The jet stream generating device according to any one of Additions 1 to 9, wherein a means of guiding the pulse laser beam into the liquid chamber is an optical fiber.

[Addition 11]

The jet stream generating device according to any one of Additions 1 to 10, further having a control part configured to change the pulse energy, pulse width and pulse repeat frequency of the pulse laser beam by the laser beam irradiation part, and variably control one, a set or all of the amount of the jet stream, the flow rate of the jet stream, and the repeat frequency of the jet stream.

[Addition 12]

The jet stream generating device according to any one of the Additions 1 to 11, wherein the liquid is water, saline solution or electrolytes, and a laser oscillator (laser device) configured to generate a holmium YAG laser (2.1 μm wavelength) as the pulse laser beam is included.

[Addition 13]

The jet stream generating device according to any one of Additions 1 to 12, wherein a calculus and a hard tissue of a living body are cut and crushed using the jet stream from the nozzle.

[Addition 14]

The jet stream generating device according to any one of Additions 1 to 13, wherein a biotissue is cut and crushed using the jet stream from the nozzle.

[Addition 15]

The jet stream generating device according to any one of Additions 1 to 14, wherein a thrombosis blocking the blood vessel is crushed using the jet stream from the nozzle.

[Addition 16]

The jet stream generating device according to any one of Additions 1 to 15, wherein the adjuster has a structure that allows to adjust the distance between a portion linked to a liquid chamber (small diameter cylindrical part) and a cylindrical part holding the optical fiber (large diameter cylindrical part).

[Addition 17]

The jet stream generating device according to Addition 16, wherein the adjuster has a rotation stopping member configured to prevent relative rotation between the portion linked to the liquid chamber (small diameter cylindrical part) and the cylindrical part holding the optical fiber (large diameter cylindrical part).

[Addition 18]

A jet stream generating method of a jet stream generating device configured to generate a jet stream of liquid, wherein the jet stream generating device has: a cylindrical liquid chamber;

a nozzle configured to open an end part of the liquid chamber and inject liquid in the liquid chamber to outside;

a liquid supply path configured to supply liquid into the liquid chamber;

a laser beam irradiation part configured to irradiate a pulse laser beam into the liquid chamber, and vaporize the liquid in the liquid chamber; and a laser oscillator configured to control laser beam intensity and laser beam pulse width independently, an inner surface of the liquid chamber has a mirror plane for reflecting and guiding the pulse laser beam emitted from the laser beam irradiation part to the end part, an adjuster configured to adjust the distance between the nozzle and the laser beam irradiation part is included, and the adjuster adjusts the distance between the nozzle and the laser beam irradiation part before or at the irradiation of the pulse laser beam by the laser beam irradiation part.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 Liquid feeding device
2 Laser device (laser oscillator)
3 Suction device
4 Control device (controller)
100 Jet stream generating device
120 Y connector (holding member)
140 Liquid supply path
160 Liquid chamber (metal cylindrical member)
165 Nozzle
170 Adjusting part (adjuster)
171 Large diameter cylindrical part (optical fiber holding member)
177 Rotation member
178 Cylindrical part (optical fiber holding member)
179 Rotation stopping member
180 Suction passage

The invention claimed is:

1. A jet stream generating device that generates a jet stream of liquid, comprising:
   a cylindrical liquid chamber;
   a nozzle that opens an end part of the liquid chamber and injects liquid in the liquid chamber to outside;
   a liquid supply path that supplies liquid into the liquid chamber;
   a laser beam irradiation part that irradiates a pulse laser beam into the liquid chamber, and vaporizes the liquid in the liquid chamber; and
   a laser oscillator that controls laser beam intensity and laser beam pulse width independently, wherein
   an inner surface of the liquid chamber comprises a mirror plane for reflecting and guiding the pulse laser beam emitted from the laser beam irradiation part to the end part, and
   the jet stream generating device further comprises an adjuster that adjusts a distance between the nozzle and the laser beam irradiation part in accordance with the pulse width of the pulse laser beam emitted from the laser beam irradiation part.

2. The jet stream generating device according to claim 1, wherein the mirror plane is a surface treated by at least one of an electrolytic polishing treatment, a reaming treatment, a plating treatment, a vapor deposition treatment, and an abrasive blowing treatment.

3. A jet stream generating method for generating a jet stream of a liquid by using a jet stream generating device that includes a cylindrical liquid chamber, a liquid supply path, a laser beam irradiation part and an adjuster, the method comprising:
   supplying the liquid into the liquid chamber through the liquid supply path;
   irradiating a pulse laser beam emitted from the laser beam irradiation part into the liquid chamber to vaporize the liquid within the liquid chamber;
   reflecting the pulse laser beam emitted from the laser beam irradiation part by a mirror plane on an inner surface of the liquid chamber to guide the pulse laser beam to an end part of the liquid chamber;
   injecting the liquid within the liquid chamber outwardly by a nozzle disposed on the end part of the liquid chamber;
   controlling laser beam density and pulse width of the pulse laser beam independently by a laser oscillator employed by the jet stream generating device;
   adjusting a distance between the nozzle and the laser beam irradiation part by the adjuster in accordance with the pulse width of the pulse laser beam emitted from the laser beam irradiation part; and
   adjusting the distance between the nozzle and the laser beam irradiation part by the adjuster before or at the irradiation of the pulse laser beam by the laser beam irradiation part.

* * * * *